United States Patent
Ben-Joseph et al.

(10) Patent No.: US 11,521,721 B2
(45) Date of Patent: *Dec. 6, 2022

(54) MEDICAL DATA AGGREGATION, TRANSFORMATION, AND PRESENTATION SYSTEM

(71) Applicant: Regard Technologies, Inc., Santa Monica, CA (US)

(72) Inventors: Eli Ben-Joseph, Santa Monica, CA (US); Nathaniel Douglas Wilson, Santa Monica, CA (US); Thomas William Moulia, Santa Monica, CA (US)

(73) Assignee: Regard Technologies, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/689,801

(22) Filed: Mar. 8, 2022

(65) Prior Publication Data

US 2022/0189595 A1 Jun. 16, 2022

Related U.S. Application Data

(63) Continuation of application No. 16/153,476, filed on Oct. 5, 2018, now Pat. No. 11,302,428.

(60) Provisional application No. 62/685,028, filed on Jun. 14, 2018.

(51) Int. Cl.
*G16H 10/60* (2018.01)
*G16H 50/20* (2018.01)
*G16H 30/40* (2018.01)

(52) U.S. Cl.
CPC ............. *G16H 10/60* (2018.01); *G16H 30/40* (2018.01); *G16H 50/20* (2018.01)

(58) Field of Classification Search
CPC ........ G16H 10/60; G16H 30/40; G16H 50/20; G06Q 50/22; G06Q 50/24
See application file for complete search history.

(56) References Cited

U.S. PATENT DOCUMENTS

2002/0193679 A1 12/2002 Malave et al.
2003/0144884 A1* 7/2003 Mayaud .................. G16Z 99/00
705/3

(Continued)

FOREIGN PATENT DOCUMENTS

WO WO-0045301 A1 * 8/2000 ........... G06F 16/957
WO WO-0045301 A1 8/2000

(Continued)

OTHER PUBLICATIONS

Lee Desiderio, Microsoft® Office—Customize the Quick Access Toolbar (IT Training Tip), Feb. 16, 2018, Bates College. (Year: 2018).*

(Continued)

*Primary Examiner* — Rachelle L Reichert
*Assistant Examiner* — Amanda R. Covington
(74) *Attorney, Agent, or Firm* — Schwegman Lundberg & Woessner, P.A.

(57) ABSTRACT

Systems and methods for medical data aggregation, transformation, and presentation are provided. In one example, a method comprises sets of attributes and supplementary attributes are selectively presented as directly editable medical notes in an interface with enhanced functionality.

19 Claims, 22 Drawing Sheets

(56) References Cited

U.S. PATENT DOCUMENTS

2008/0313547 A1 12/2008 Wallis et al.
2019/0385714 A1 12/2019 Ben-Joseph et al.

FOREIGN PATENT DOCUMENTS

WO     WO-2000045301        8/2000
WO     WO-2019240950 A1   12/2019

OTHER PUBLICATIONS

"U.S. Appl. No. 16/153,476, Advisory Action dated Jun. 10, 2021", 2 pgs.
"U.S. Appl. No. 16/153,476, Examiner Interview Summary dated Jun. 1, 2021", 2 pgs.
"U.S. Appl. No. 16/153,476, Final Office Action dated Mar. 30, 2021", 15 pgs.
"U.S. Appl. No. 16/153,476, Non Final Office Action dated Dec. 8, 2020", 17 pgs.
"U.S. Appl. No. 16/153,476, Notice of Allowance dated Dec. 6, 2021", 16 pgs.
"U.S. Appl. No. 16/153,476, Response filed Mar. 8, 2021 to Non Final Office Action dated Dec. 8, 2020", 14 pgs.
"U.S. Appl. No. 16/153,476, Response filed Jun. 1, 2021 to Final Office Action dated Mar. 30, 201", 15 pgs.
"International Application Serial No. PCT/US2019/034369, International Preliminary Report on Patentability dated Dec. 24, 2020", 6 pgs.
"International Application Serial No. PCT/US2019/034369, International Search Report dated Sep. 19, 2019", 2 pgs.
"International Application Serial No. PCT/US2019/034369, Written Opinion dated Sep. 19, 2019", 4 pgs.
Kaufman, Lori, "How to View Multiple Documents at Once in Word", howtogeek.com, (Jun. 30, 2015).
Lee, Desiderio, "Microsoft® Office—Customize the Quick Access Toolbar (IT Training Tip)", Bates College, (Feb. 16, 2018).

* cited by examiner

602 — HYPOKALEMIA                                                           600

604 { IN A NUTSHELL, LOW POTASSIUM VALUES. OCCURS BECAUSE OF CELLULAR RE-DISTRIBUTION, KIDNEY OR GI TRACT LOSSES, DECREASED INTAKE.

606 { ICD10: E87.6
      ICD9: 276.8

608 { DIAGNOSIS:
      GET THE LAB VALUE FROM [CMP/BMP/RENAL FUNCTION TEST] WITHIN THE LAST 24 HOURS
      K < 3.5

610 { NOTE.PROPERTIES:
         A. 3.0 < MILD TO MODERATE < 3.4
         B. SEVERE < 3.0

DOCUMENTATION:
   NOTE.ASSESSMENT:
      • THE POTASSIUM VALUE AND THE DATE THE TEST WAS TAKEN
            A. LABEL "PSEUDOHYPOKALEMIA" IF WBC > 100 WITHIN 24 HOURS OF THE
               POTASSIUM LAB AND END DOCUMENTATION THERE: USE 'WHITE
               BLOOD CELL COUNT'
      • CONSIDER HOLDING ALL ACTIVE DIURETICS THAT PATIENT IS ACTIVELY TAKING WHICH MAY BE
        CONTRIBUTING TO HYPOKALEMIA:

612 {
         • CHLOROTHIAZIDE (DIURIL)
         • CHLORTHALIDONE
         • HYDROCHLOROTHIAZIDE (MICROZIDE)
         • INDAPAMIDE
         • METOLAZONE
         • BUMETANIDE (BUMEX)
         • ETHACRYNIC ACID (EDECRIN)
         • FUROSEMIDE (LASIX)
         • TORSEMIDE (DEMADEX)

614 { NOTE.GENERAL
         • IF LOW PHOSPHATE SHOW LOW PHOSPHATE LAB VALUE AND DATE
         • IF LOW MAGNESIUM SHOW LOW MAGNESIUM LAB VALUE AND DATE

616 — CHART: SHOWS POTASSIUM, MAGNESIUM AND PHOSPHORUS VALUES

*Fig. 6A*

618 { NOTE.PLAN:
  • RECOMMEND REPLACING ELECTROLYTE FOR LOW K, pH, AND Mg

620 {
LAB ID FOR:

POTASSIUM:
POTASSIUM (POC)
POTASSIUM, PLASMA

MAGNESIUM:
MAGNESIUM

PHOSPHATE:
PHOSPHORUS

DO HYPO/HYPER- MAGNESEMIA AND PHOSPHATEMIA

ISSUES:
CONVERT LAB ID UNITS TO STANDARD REPORTED UNITS FOR ALL UNIT TYPES

622 { MAGNESIUM
  — mg/dL AND mmol/L

*Fig. 6B*

702 — RESPIRATORY FAILURE Dx

704 — BACKGROUND

- 706 — • MACHINE NAME: RESP_FAILURE
- 708 — • HUMAN-READABLE NAME: RESPIRATORY FAILURE
- • POSITIVE DIAGNOSES:
  - 710 {
    - ○ HYPOXEMIC RESPIRATORY FAILURE
    - ○ HYPERCAPNEIC RESPIRATORY FAILURE
    - ○ HYPOXEMIC AND HYPERCAPNEIC RESPIRATORY FAILURE
    - ○ ACUTE / CHRONIC / ACUTE ON CHRONIC
- 712 {
  - • ICD CODES:
    - ○ ACUTE
      - ▪ HYPOXEMIC:
      - ▪ HYPERCAPNEIC:
      - ▪ BOTH:
    - ○ CHRONIC
      - ▪ HYPOXEMIC:
      - ▪ HYPERCAPNEIC:
      - ▪ BOTH:
    - ○ ACUTE ON CHRONIC
      - ▪ HYPOXEMIC:
      - ▪ HYPERCAPNEIC:
      - ▪ BOTH:

714 — DIAGNOSTIC PATHWAY

- 716 {
  - • CHECK $PaO_2$ AND $PaCO_2$ LAB VALUES FROM MOST RECENT ABG TAKEN WITHIN 48 HOURS
    - ○ $PaO_2 < 55$: HYPOXEMIC
    - ○ $PaCO_2 > 40$: HYPERCAPNEIC

- 718 {
  - • DETERMINE IF ACUTE, CHRONIC OR ACUTE AND CHRONIC
    - ○ LOOK IN AKI MODULE
    - ○ CHRONIC HYPERCAPNEIC RF CAUSES KIDNEYS TO COMPENSATE FOR ACIDOSIS; ACUTE-ON-CHRONIC CAN BE DETECTED THROUGH HIGHER-THAN-BASELINE $PaCO_2$ PLUS pH NO LONGER COMPENSATED TO NORMAL (7.35-7.45) RANGE

- 720 {
  - • INCLUDE POSSIBLE CAUSES
    - ○ HYPOXEMIC: PNEUMONIA, ACETELECTASIS, CHF, ARDS
    - ○ HYPERCAPNEIC: DECREASED RESPIRATORY DRIVE FROM SEDATIVES; RESPIRATORY MUSCLE WEAKNESS FROM NEURO-MUSCULAR DISEASE, SCOLIOSIS; OBSTRUCTIVE LUNG DISEASES LIKE ASTHMA, COPD, ARDS

*Fig. 7A*

722 — NOTE

724 {
- NAME: (HYPOXEMIC / HYPERCAPNEIC / HYPOXEMIC AND HYPERCAPNEIC) RESPIRATORY FAILURE
  - INCLUDE ACUTE/CHRONIC/ACUTE ON CHRONIC IN NAME

726 {
- ASSESSMENT
  - ADD CHART: LOOK AT ACID_BASE MODULE. USE DATA FOR THE PAST WEEK, IF THERE'S > 1 DATA POINT.

728 {
- PLAN
  - MONITOR
  - ADD DRUGS WITH UTIL FUNCTION

730 {
- GENERAL
  - POSSIBLE CAUSES

Fig. 7B

| HEALTHTENSOR | NOTE | RECORD |

X.X. IS A 62 YEAR OLD WOMAN WITH A HISTORY OF CHRONIC KIDNEY INJURY STAGE 5, EMPHYSEMA, T2DM, HLD, HTN, OVERWEIGHT, AND CHRONIC CHF PRESENTING WITH ACUTE ON CHRONIC CHF

CONGESTIVE HEART FAILURE: SUSPECT ACUTE ON CHRONIC COMBINED SYSTOLIC AND DIASTOLIC
- ELEVATED BNP 492.0 PG/ML (10/16/15) ~816A
- CONTINUE CARVEDILOL 10 mG PO qDAY ~816
- HOME MEDICATIONS BEING HELD: METOPROLOL ~816
- STRICT I/O'S ~816
- DAILY WEIGHTS ~816

CHRONIC KIDNEY INJURY STAGE 5
- AVOID NEPHROTOXIC AGENTS ~818
- MONITOR ~818

PULMONARY DISEASE

DIABETES MELLITUS, TYPE 2: UNCONTROLLED
- MOST RECENT HEMOGLOBIN A1c: 8.6% (3/18/15  5:50PM)
- BLOOD GLUCOSE OVER THE LAST 24 HOURS ELEVTED (>180 mG/AL) ~820
- CONTINUE INSULIN LISPRO 10 mG PO qDAY
- CONTINUE NATEGLINIDE 10 mG PO qDAY
- CONTINUE INSULIN NPH/REGULAR 70/30 10 mG PO qDAY
- CONTINUE PREGABALIN 10 mG PO qDAY
- CONTINUE PMETFORMIN 10 mG PO qDAY
- CONTINUE TOLBUTAMIDE 10 mG PO qDAY ~820
- CONTINUE INSULIN ASPART 10 mG PO qDAY
- RECOMMEND STARTING HOME MEDICATIONS
- MONITOR

HYPERLIPIDEMIA: WITH HISTORY OF CLINICAL ASCVD
- CONTINUE TOLBUTAMIDE 10 mG PO qDAY
- CONSIDER INITIATING HIGH-INTENSITY STATINS, IF TOLERATED

HYPERTENSION: CURRENTLY HYPOTENSIVE
- MOST RECENT BP: 103/60 MMHG (10/16/15 9:00PM) ~870
- 24HR BP RANGE: (52-128)/(25-98) mmHG ~872
- CONTINUE CARVEDILOL 10 mG PO qDAY

Fig. 8A

HEALTHTENSOR NOTE RECORD

X.X. IS A 62 YEAR OLD WOMAN WITH A HISTORY OF CHRONIC KIDNEY INJURY STAGE 5, EMPHYSEMA, T2DM, HLD, HTN, OVERWEIGHT, AND CHRONIC CHF PRESENTING WITH ACUTE ON CHRONIC CHF

CONGESTIVE HEART FAILURE: SUSPECT ACUTE ON CHRONIC COMBINED SYSTOLIC AND DIASTOLIC
- ELEVATED BNP 492.0 PG/ML (10/16/15)
- CONTINUE CARVEDILOL 10 mG PO qDAY
- HOME MEDICATIONS BEING HELD: METOPROLOL
- STRICT I/O'S
- DAILY WEIGHTS  } 814

CHRONIC KIDNEY INJURY STAGE 5
- AVOID NEPHROTOXIC AGENTS
- MONITOR  } 816

PULMONARY DISEASE  } 806

DIABETES MELLITUS, TYPE 2: UNCONTROLLED
- MOST RECENT HEMOGLOBIN A1c: 8.6% (3/18/15 5:50PM)
- BLOOD GLUCOSE OVER THE LAST 24 HOURS ELEVTED (>180 mG/AL)
- CONTINUE INSULIN LISPRO 10 mG PO qDAY
- CONTINUE NATEGLINIDE 10 mG PO qDAY
- CONTINUE INSULIN NPH/REGULAR 70/30 10 mG PO qDAY
- CONTINUE PREGABALIN 10 mG PO qDAY
- CONTINUE PMETFORMIN 10 mG PO qDAY
- CONTINUE TOLBUTAMIDE 10 mG PO qDAY
- CONTINUE INSULIN ASPART 10 mG PO qDAY
- RECOMMEND STARTING HOME MEDICATIONS
- MONITOR

HYPERLIPIDEMIA: WITH HISTORY OF CLINICAL ASCVD
- CONTINUE TOLBUTAMIDE 10 mG PO qDAY
- CONSIDER INITIATING HIGH-INTENSITY STATINS, IF TOLERATED

HYPERTENSION: CURRENTLY HYPOTENSIVE
- MOST RECENT BP: 103/60 MMHG (10/16/15 9:00PM)
- 24HR BP RANGE: (52-128)/(25-98) mmHG
- CONTINUE CARVEDILOL 10 mG PO qDAY

850 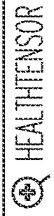

*Fig. 8B*

HEALTHTENSOR                                                    NOTE  RECORD

X.X. IS A 62 YEAR OLD WOMAN WITH A HISTORY OF CHRONIC KIDNEY INJURY STAGE 5, EMPHYSEMA, T2DM, HLD, HTN, OVERWEIGHT, AND CHRONIC CHF PRESENTING WITH ACUTE ON CHRONIC CHF

CONGESTIVE HEART FAILURE: SUSPECT ACUTE ON CHRONIC COMBINED SYSTOLIC AND DIASTOLIC
- ELEVATED BNP 492.0 PG/ML (10/16/15)
- CONTINUE CARVEDILOL 10 mG PO qDAY
- HOME MEDICATIONS BEING HELD: METOPROLOL
- STRICT I/O'S
- DAILY WEIGHTS

CHRONIC KIDNEY INJURY STAGE 5
- AVOID NEPHROTOXIC AGENTS
- MONITOR

PULMONARY DISEASE

DIABETES MELLITUS, TYPE 2: UNCONTROLLED
- MOST RECENT HEMOGLOBIN A1c: 8.6% (3/18/15  5:50PM)
- BLOOD GLUCOSE OVER THE LAST 24 HOURS ELEVTED (>180 mG/AL)
- CONTINUE INSULIN LISPRO 10 mG PO qDAY
- CONTINUE NATEGLINIDE 10 mG PO qDAY
- CONTINUE INSULIN NPH/REGULAR 70/30 10 mG PO qDAY
- CONTINUE PREGABALIN 10 mG PO qDAY
- CONTINUE PMETFORMIN 10 mG PO qDAY
- CONTINUE TOLBUTAMIDE 10 mG PO qDAY
- CONTINUE INSULIN ASPART 10 mG PO qDAY
- RECOMMEND STARTING HOME MEDICATIONS
- MONITOR

HYPERLIPIDEMIA: WITH HISTORY OF CLINICAL ASCVD
- CONTINUE TOLBUTAMIDE 10 mG PO qDAY
- CONSIDER INITIATING HIGH-INTENSITY STATINS, IF TOLERATED

HYPERTENSION: CURRENTLY HYPOTENSIVE
- MOST RECENT BP: 103/60 MMHG (10/16/15  9:00PM)
- 24HR BP RANGE: (52-128)/(25-98) mmHg
- CONTINUE CARVEDILOL 10 mG PO qDAY

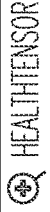

802 — X.X. IS A 62 YEAR OLD WOMAN WITH A HISTORY OF CHRONIC KIDNEY INJURY STAGE 5, EMPHYSEMA, T2DM, HLD, HTN, OVERWEIGHT, AND CHRONIC CHF PRESENTING WITH ACUTE ON CHRONIC CHF

CONGESTIVE HEART FAILURE: SUSPECT ACUTE ON CHRONIC COMBINED SYSTOLIC AND DIASTOLIC
- ELEVATED BNP 492.0 PG/ML (10/16/15) ~ 924
- PREVIOUS DIAGNOSIS OF HEART FAILURE
- CONTINUE CARVEDILOL 10 mG PO qDAY
- HOME MEDICATIONS BEING HELD: METOPROLOL
- STRICT I/O'S
- DAILY WEIGHTS

CHRONIC KIDNEY INJURY STAGE 5 ~ 804
- GFR <60ML/MIN/1.73M^2 FOR MORE THAN 3 MONTHS ~ 924AA
- PREVIOUS DIAGNOSIS OF CHRONIC RENAL DISEASE ~ 924AB
- ESTIMATED GFR RANGE IS 0-15 ML/MIN/1.73M^2 FROM CR BASLINE OF 6.9 MG/DL ~ 924AC
- BASELINE CREATININE OF 6.9 MG/DL ~ 924AD
- AVOID NEPHROTOXIC AGENTS ~ 818
- MONITOR ~ 818

850 ~ [x ∧ ≡]
922

806 ~ PULMONARY DISEASE
- PREVIOUS DIAGNOSIS: CHRONIC OBSTRUCTIVE PULMONARY DISEASE (UNSPECIFIED), OTHER EMPHYSEMA, CHRONIC OBSTRUCTIVE PULMONARY DISEASE WITH ACUTE LOWER RESPIRATORY INFECTION ~ 926

808 ~ DIABETES MELLITUS, TYPE 2: UNCONTROLLED
  MOST RECENT HEMOGLOBIN A1c: 8.6% (3/18/15 5:50PM)
  BLOOD GLUCOSE OVER THE LAST 24 HOURS ELEVTED (>180 mG/dL)
- CONTINUE INSULIN LISPRO 10 mG PO qDAY
- CONTINUE NATEGLINIDE 10 mG PO qDAY
- CONTINUE INSULIN NPH/REGULAR 70/30 10 mG PO qDAY
- CONTINUE PREGABALIN 10 mG PO qDAY
- CONTINUE METFORMIN 10 mG PO qDAY
- CONTINUE TOLBUTAMIDE 10 mG PO qDAY
- CONTINUE INSULIN ASPART 10 mG PO qDAY
- RECOMMEND STARTING HOME MEDICATIONS
- MONITOR

810 ~ HYPERLIPIDEMIA: WITH HISTORY OF CLINICAL ASCVD
  CONTINUE TOLBUTAMIDE 10 mG PO qDAY
  CONSIDER INITIATING HIGH-INTENSITY STATINS, IF TOLERATED

*Fig. 10*

⊕ HEALTHTENSOR | NOTE RECORD

ENCOUNTER: 5289822

NOTES  LABS  VITALS  MEDS  IMAGING

23:13:00 20:57:30 19:07:30 13:58:00 13:38:30 09:06:10 08:25:00 13:14:00 08:36:00 22:14:00 19:22:00 15:33:00 09:10:30 08:35:00
10/16/2015 10/16/2015 10/16/2015 10/16/2015 10/16/2015 10/16/2015 10/16/2015 09/17/2015 09/17/2015 09/16/2015 09/16/2015 09/16/2015 09/16/2015 09/16/2

WBC MORPHOLOGY

STATUS OF UNIT

UROBILINOGEN

UPAC

UPPN

UPTA

UPUR

BLAST

UNIT NUMBER

HEALTHTENSOR — NOTE RECORD

ENCOUNTER: 5289822

| NOTES | LABS | VITALS | MEDS | IMAGING | | | | | | | | | | | |
|---|---|---|---|---|---|---|---|---|---|---|---|---|---|---|---|
| | 21:00:00 10/16/2015 | 20:00:00 10/16/2015 | 19:00:00 10/16/2015 | 17:45:00 10/16/2015 | 17:30:00 10/16/2015 | 17:20:00 10/16/2015 | 17:15:00 10/16/2015 | 17:00:00 10/16/2015 | 16:00:00 10/16/2015 | 13:00:00 10/16/2015 | 11:00:00 10/16/2015 | 10:00:00 10/16/2015 | 09:00:00 10/16/2015 | 07:00:00 10/16/2015 | 06:00:00 10/16/2015 |
| SpO2 | 95 | 96 | 93 | 92 | | 95 | 92 | 99 | 96 | 99 | 99 | 100 | 99 | 97 | 98 |
| CARDIAC RHYTHM | NSR | | | | | | | | | | | | NSR | | NSR PVC |
| BP | 103/60 | 102/71 | 109/74 | 94/61 | 84/57 | 52/43 | 79/54 | | 110/59 | 110/53 | 120/66 | 104/53 | 104/57 | 116/60 | 115/51 |
| TEMP | 98 | | | | | | | 97.5 | | 98.1 | | | 98.5 | | 98.7 |
| PULSE | 83 | 75 | 72 | 71 | 77 | 76 | 83 | 82 | 82 | 92 | 85 | 74 | 76 | 85 | 86 |
| RESP RATE OBSERVED | | | | | | | | | | | | | | | |
| RESP | 19 | | 15 | 15 | 19 | 14 | 20 | 20 | 20 | 23 | 25 | 18 | 19 | 22 | 21 |

*Fig. 12*

⊕ HEALTHTENSOR | NOTE  RECORD

ENCOUNTER: 5289822

NOTES  LABS  VITALS  MEDS  IMAGING

| NAME | START | END |
|---|---|---|
| INSULIN LISPRO | 2015-10-16 18 30 00-00 00 | 2015-10-17 08 30 00-00 00 |
| NATEGLINIDE | 2015-10-16 18 30 00-00 00 | 2015-10-17 08 30 00-00 00 |
| INSULIN NPH/REGULAR 70/30 | 2015-10-16 12 30 00-00 00 | 2015-10-17 08 30 00-00 00 |
| PREGABALIN | 2015-10-16 12 30 00-00 00 | 2015-10-17 08 30 00-00 00 |
| METFORMIN | 2015-10-16 12 30 00-00 00 | 2015-10-17 08 30 00-00 00 |
| TOLBUTAMIDE | 2015-10-15 08 00 00-00 00 | 2015-10-17 08 30 00-00 00 |
| CARVEDILOL | 2015-10-15 08 00 00-00 00 | 2015-10-18 20 00 00-00 00 |
| INSULIN ASPART | 2015-10-16 08 00 00-00 00 | 2015-10-18 20 00 00-00 00 |

⊕ HEALTHTENSOR | NOTE  RECORD

ENCOUNTER: 5289822

NOTES    LABS    VITALS    MEDS    IMAGING

PATIENT HAS NO IMAGES

Fig. 13

MEDICAL DATA AGGREGATION, TRANSFORMATION, AND PRESENTATION SYSTEM

CROSS-REFERENCE TO RELATED APPLICATIONS

This patent application is a continuation of U.S. patent application Ser. No. 16/153,476, filed Oct. 5, 2018, entitled MEDICAL DATA AGGREGATION, TRANSFORMATION, AND PRESENTATION SYSTEM" which claims the benefit of U.S. Provisional Patent Application No. 62/685,028, filed Jun. 14, 2018, entitled "MEDICAL DATA AGGREGATION, TRANSFORMATION, AND PRESENTATION SYSTEM", which are incorporated by reference herein in their entirety.

TECHNICAL FIELD

The subject matter disclosed herein generally relates to a medical data aggregation, transformation, and presentation system. In one aspect, this disclosure relates to computing apparatus with an improved user interface for medical diagnostic workflows.

BACKGROUND

The present disclosure seeks to address technical problems existing in the analysis of medical data and generation of accurate documentation of clinical findings. Studies have shown that for every hour a physician spends with patients they spend two hours with the electronic health record in an effort to make sense of or discern trends in disparate sets of information or disjointed patient data and generate appropriate documentation for their diagnoses, assessments and plans of care. Current approaches and tools increase the burden and time requirements on providers as they manage and review patient data. Similarly, patients and patient care suffers because providers must spend time reviewing and documenting patient data. There are very few tools today that help providers manage their data in a meaningful way, if at all. At best, present systems are a significant inconvenience. At worst, lack of access to actionable data, or conversely data overload, can bury symptoms and cause misdiagnosis, malpractice, and negative patient outcomes like premature death.

BRIEF SUMMARY

Thus, in some embodiments, there is provided a computing apparatus, the computing apparatus comprising a processor; and a memory storing instructions that, when executed by the processor, configure the apparatus to access first patient data relating to a first medical condition, the first patient data including a first set of attributes relating to the first medical condition; access second patient data relating to a second medical condition, the second patient data including a second set of attributes relating to the second medical condition; combine the first and second patient data into a patient data structure that includes the first and second sets of attributes relating to the first and second medical condition; generate first and second sets of supplementary attributes relating to the respective first and second sets of attributes; generate a user interface; cause presentation of the first and second sets of attributes relating to the first and second medical conditions as notes in the user interface, wherein the presentation comprises: presentation, in a first display zone of the user interface, a first view including at least one attribute from the first set of attributes relating to the first medical condition; presentation, in a second display zone of the user interface, a first supplementary view including at least one supplementary attribute from the first set of supplementary attributes relating to the first medical condition; and presentation of a toggle feature selectable to toggle between the presentations of the first view and the first supplementary view.

In some examples, the presentation further comprises presentation, in a third display zone of the user interface, a third view including at least one attribute from the second set of attributes relating to the second medical condition, and wherein the toggle element is configured to appear to move, under the input or guidance of a pointing device, between respective locations at or adjacent the first and third display zones of the user interface.

In some examples, the presentation further comprises presentation, in a fourth display zone of the user interface, a second supplementary view including at least one supplementary attribute from the second set of supplementary attributes relating to the second medical condition, and wherein the toggle element is configured to toggle, at each respective location, between the presentations of the first view and the first supplementary view, and the second view and second supplementary view, respectively.

In some examples, the notes are directly editable by a user in the user interface to edit at least one of the first, first supplementary, second, and second supplementary views. In some examples, the first, first supplementary, second, and second supplementary views are visible simultaneously in the user interface.

In some examples, the first or second supplementary view includes a graph depicting aspects relating to an attribute or supplementary attribute of the first or second medical condition In some examples, the graph includes a time-based representation of a medication regimen, the time-based representation temporally synchronous with the depicted aspect relating to the attribute or supplementary attribute of the first or second medical condition.

In some examples, combining the first and second patient data into a patient data structure includes, at least extracting attribute data from a table based on an assigned relevance of that data to a diagnosis of a medical condition; correlating the extracted attribute data with a report in a diagnostic report; and generating a supplementary attribute by identifying a narrative or date stamp associated with the image based on the medical condition.

BRIEF DESCRIPTION OF THE DRAWINGS

Some embodiments are illustrated by way of example and not limitation in the figures of the accompanying drawings. In order to identify more easily the discussion of any particular element or act, the most significant digit or digits in a reference number refer to the figure number in which that element is first introduced.

FIGS. 6A-6B show a flowchart for a method, in accordance with an example embodiment.

FIGS. 7A-7B show a flowchart for a method, in accordance with an example embodiment.

FIGS. 8A-8C show an example user interface, in accordance with an example embodiment.

FIG. 9 shows a view in an example user interface, in accordance with an example embodiment.

FIG. 10 shows an example Labs view in an example user interface, in accordance with an example embodiment.

FIG. 12 shows an example Meds view in an example user interface, in accordance with an example embodiment.

FIG. 13 shows an example Imaging view in an example user interface, in accordance with an example embodiment.

DETAILED DESCRIPTION

Figure 1:
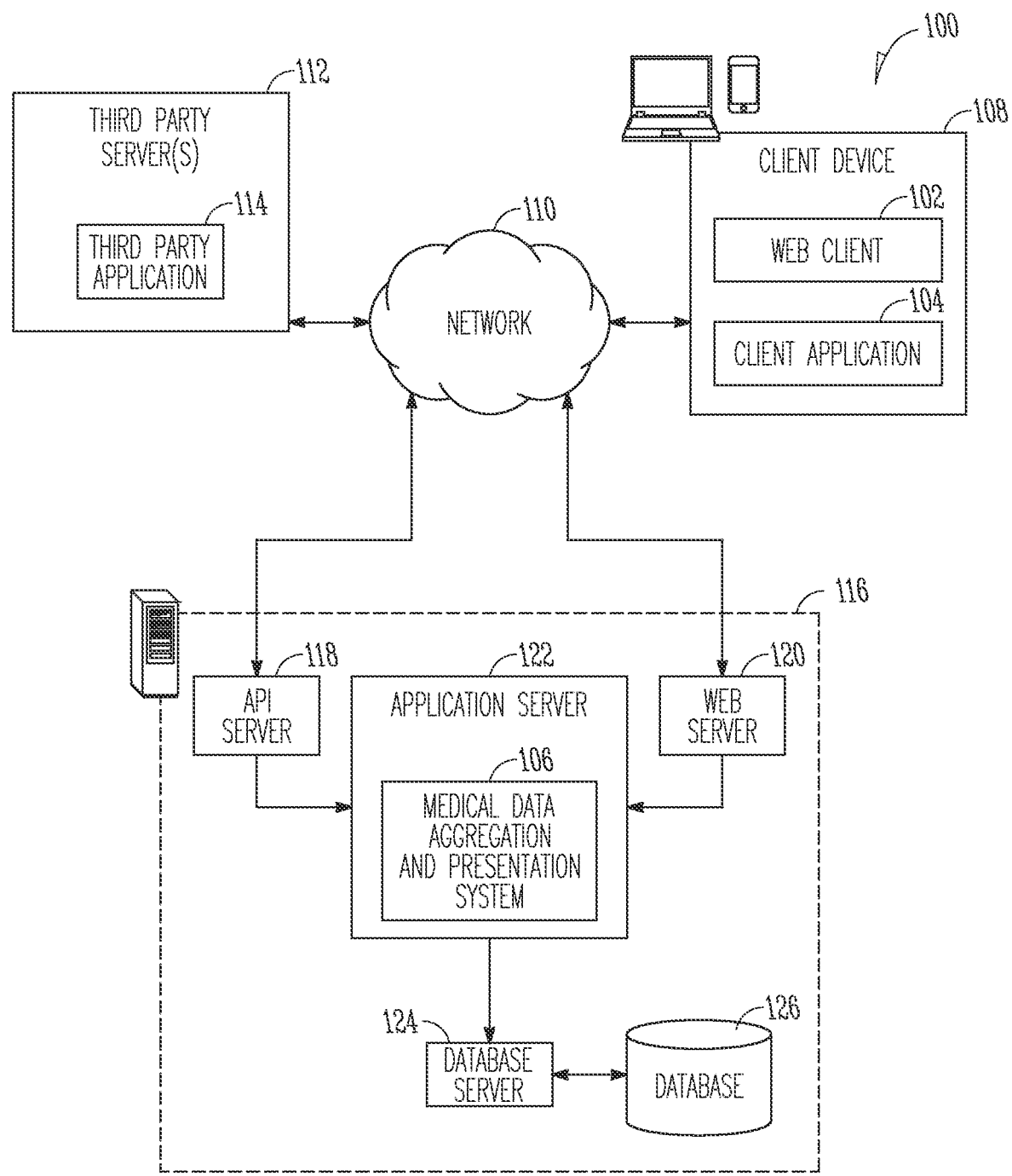
FIG. 1 is a block diagram illustrating a networked system, according to an example embodiment.

"Carrier Signal" in this context refers to any intangible medium that is capable of storing, encoding, or carrying instructions for execution by the machine, and includes digital or analog communications signals or other intangible medium to facilitate communication of such instructions. Instructions may be transmitted or received over the network using a transmission medium via a network interface device and using any one of a number of well-known transfer protocols.

"Client Device" or "Electronic Device" in this context refers to any machine that interfaces to a communications network to obtain resources from one or more server systems or other client devices. A client device may be, but is not limited to, a mobile phone, desktop computer, laptop, portable digital assistants (PDAs), smart phones, tablets, ultra-books, netbooks, laptops, multi-processor systems, microprocessor-based or programmable consumer electronics, game consoles, set-top boxes, or any other communication device that a user may use to access a network.

"Communications Network" in this context refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"Component" in this context refers to a device, physical entity, or logic having boundaries defined by function or subroutine calls, branch points, application program interfaces (APIs), or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components.

A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors.

It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component"(or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"Machine-Readable Medium" in this context refers to a component, device or other tangible media able to store instructions and data temporarily or permanently and may include, but not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium, or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"Processor" in one context refers to any circuit or virtual circuit (a physical circuit emulated by logic executing on an actual processor) that manipulates data values according to control signals (e.g., "commands", "op codes", "machine code", etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as "cores") that may execute instructions contemporaneously.

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and shown in the drawings that form a part of this document: Copyright 2018, HealthTensor, Inc., All Rights Reserved.

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

In a not uncommon scenario, a doctor may arrive to do hospital rounds at say, 9 a.m. on a given day. The doctor's patient has, for example, been in the hospital for three-plus days. The last time the doctor did a round on the patient was 9:00 p.m. the previous night. So, twelve hours of data have come in since the patient was last seen, and it is now the doctor's duty and responsibility as a doctor to review the new data in detail to understand how that changes, if at all, the current assessment of the patient. This involves creating new diagnoses, updating current ones, and looking at possible trends that may be informing the identification of hidden medical conditions.

Typically, it takes 10 to 30 minutes of hurried review time for the doctor to review that data to understand the updates presented and then to type up or modify manually bed notes (or "history") based on the doctor's findings. Oftentimes, many different data sets, blood results, lab work, and different charts are presented. Everything is disjointed. For example, a graph of blood results may be provided quite separately from any treatment history underpinning an illustrated trend, or quite separately from information identifying a patient's allergies. Similarly, medication data is provided independently of anything else. It is presently extremely time-consuming, and inconvenient for a doctor to go through and assimilate the new data and form an overall view and diagnosis of a patient's condition. The present inventive subject matter seeks to address these problems by providing a technologically improved medical data aggregation and presentation system, and a highly interactive and functional user interface.

With reference to FIG. 1, an example embodiment of a high-level SaaS network architecture 100 is shown. A networked system 116 provides server-side functionality via a network 110 (e.g., the Internet or wide area network (WAN)) to a client device 108. A web client 102 and a programmatic client, in the example form of a client application 104, are hosted and execute on the client device 108. The networked system 116 includes an application server 122, which in turn hosts a medical data aggregation and presentation system 106 that provides a number of functions and services to the application 104 that accesses the networked system 116. The application 104 also provides a number of user interfaces described herein, which present output of certain operations as described herein to a user of the client device 108.

The client device 108 enables a user to access and interact with the networked system 116, and ultimately with the medical data aggregation and presentation system 106. For instance, the user provides input (e.g., touch screen input or alphanumeric input) to the client device 108, and the input is communicated to the networked system 116 via the network 110. In this instance, the networked system 116, in response to receiving the input from the user, communicates information back to the client device 108 via the network 110 to be presented to the user.

An Application Program Interface (API) server 118 and a web server 120 are coupled, and provide programmatic and web interfaces respectively, to the application server 122. The application server 122 hosts the medical data aggregation and presentation system 106, which includes components or applications described further below. The application server 122 is, in turn, shown to be coupled to a database server 124 that facilitates access to information storage repositories (e.g., a database 126). In an example embodiment, the database 126 includes storage devices that store information accessed and generated by the medical data aggregation and presentation system 106.

Additionally, a third-party application 114, executing on a third-party server(s) 112, is shown as having programmatic access to the networked system 116 via the programmatic interface provided by the Application Program Interface (API) server 118. For example, the third-party application 114, using information retrieved from the networked system 116, may support one or more features or functions on a website hosted by the third party.

Turning now specifically to the applications hosted by the client device 108, the web client 102 may access the various systems (e.g., the medical data aggregation and presentation system 106) via the web interface supported by the web server 120. Similarly, the application 104 (e.g., an "app" such as a HealthTensor app) accesses the various services and functions provided by the medical data aggregation and presentation system 106 via the programmatic interface provided by the Application Program Interface (API) server 118. The application 104 may be, for example, an "app" executing on a client device 108, such as an iOS or Android OS application to enable a user to access and input data on the networked system 116 in an off-line manner, and to perform batch-mode communications between the programmatic client application 104 and the networked system networked system 116.

Further, while the SaaS network architecture 100 shown in FIG. 1 employs a client-server architecture, the present inventive subject matter is of course not limited to such an architecture, and could equally well find application in a distributed, or peer-to-peer, architecture system, for example. The medical data aggregation and presentation system 106 could also be implemented as a standalone software program, which does not necessarily have networking capabilities.

Figure 2:
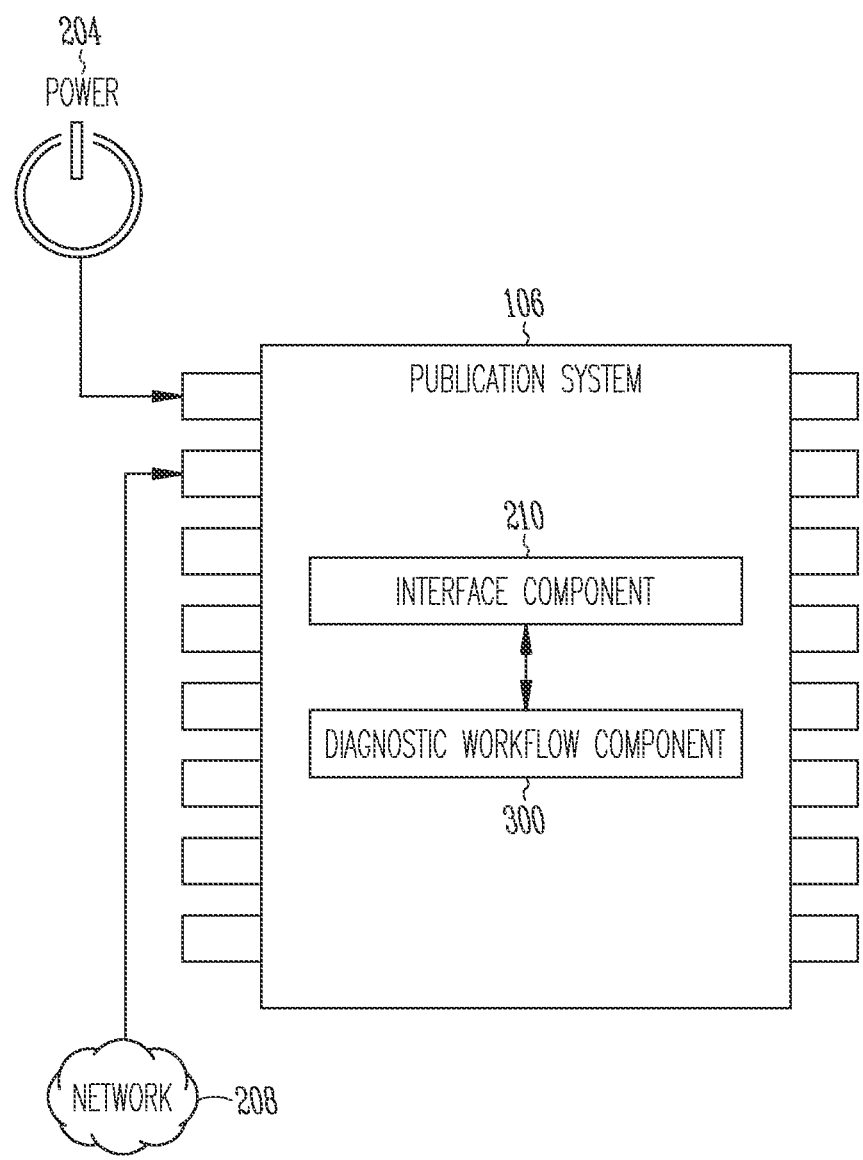
FIG. 2 is a block diagram showing the architectural aspects of a networked system, according to some example embodiments.

FIG. 2 is a block diagram showing architectural details of the medical data aggregation and presentation system 106, according to some example embodiments. Specifically, the medical data aggregation and presentation system 106 is shown to include an interface component 210 by which the medical data aggregation and presentation system 106 communicates (e.g., over the network 208) with other systems within the SaaS network architecture 100.

The interface component 210 is communicatively coupled to a diagnostic workflow component 300 that operates to provide diagnostic workflows in accordance with the methods described herein with reference to the accompanying drawings.

Figure 3:
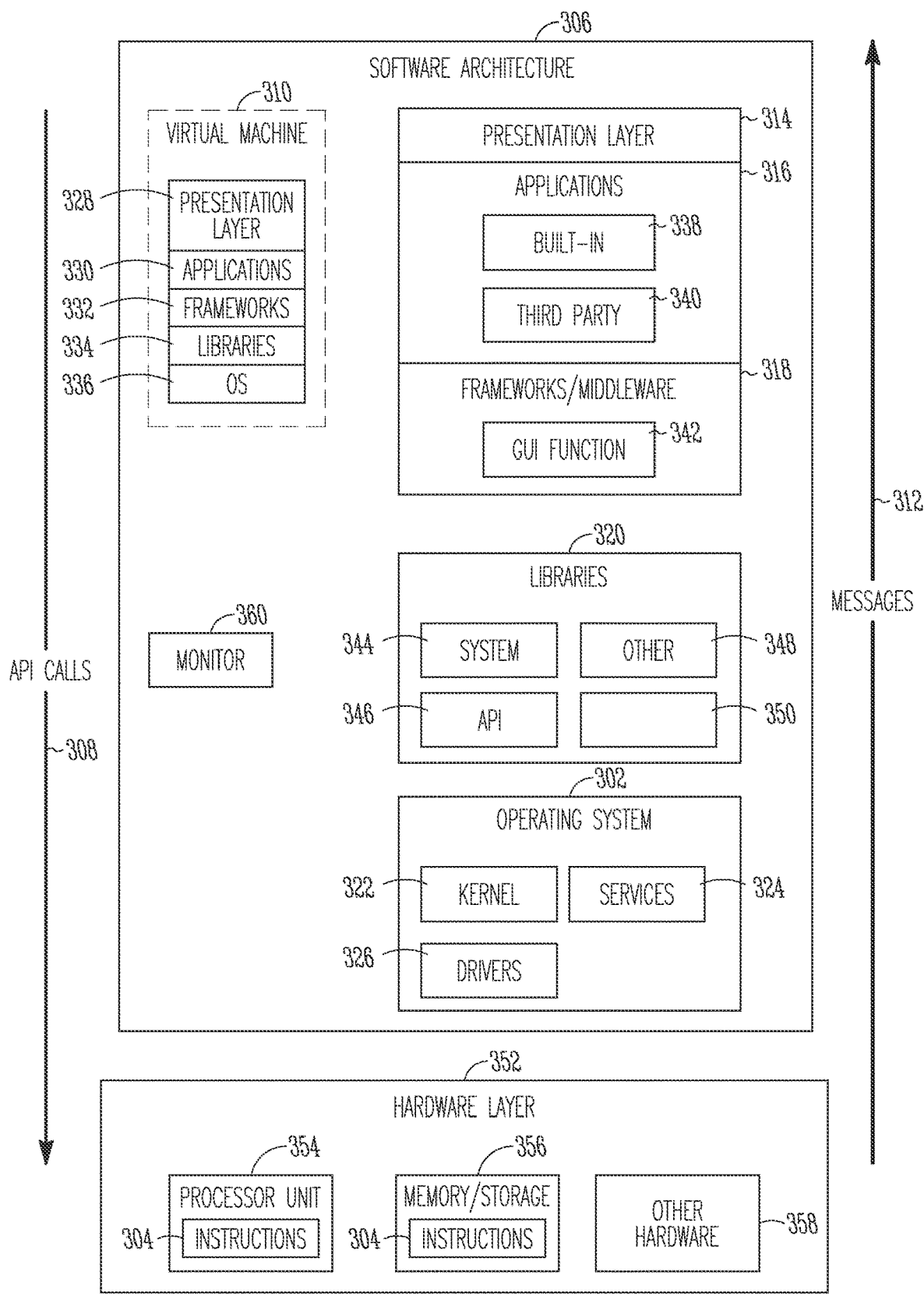
FIG. 3 is a block diagram illustrating a representative software architecture, which may be used in conjunction with various hardware architectures herein described.

FIG. 3 is a block diagram illustrating an example software architecture 306, which may be used in conjunction with various hardware architectures herein described. FIG. 3 is a non-limiting example of a software architecture 306 and it will be appreciated that many other architectures may be implemented to facilitate the functionality described herein. The software architecture 306 may execute on hardware such as machine 400 of FIG. 4 that includes, among other things, processors 404, memory/storage 406, and I/O components 418. A representative hardware layer 352 is illustrated and can represent, for example, the machine 400 of FIG. 4. The representative hardware layer 352 includes a processing unit 354 having associated executable instructions 304. Executable instructions 304 represent the executable instructions of the software architecture 306, including implementation of the methods, components and so forth described herein. The hardware layer 352 also includes memory and/or storage modules as memory/storage 356, which also have executable instructions 304. The hardware layer 352 may also comprise other hardware 358.

In the example architecture of FIG. 3, the software architecture 306 may be conceptualized as a stack of layers where each layer provides particular functionality. For example, the software architecture 306 may include layers such as an operating system 302, libraries 320, applications 316 and a presentation layer 314. Operationally, the applications 316 and/or other components within the layers may invoke application programming interface (API) API calls 308 through the software stack and receive a response as messages 312 in response to the API calls 308. The layers illustrated are representative in nature and not all software architectures have all layers. For example, some mobile or special purpose operating systems may not provide a frameworks/middleware 318, while others may provide such a layer. Other software architectures may include additional or different layers.

The operating system 302 may manage hardware resources and provide common services. The operating system 302 may include, for example, a kernel 322, services 324, and drivers 326. The kernel 322 may act as an abstraction layer between the hardware and the other software layers. For example, the kernel 322 may be responsible for memory management, processor management (e.g., scheduling), component management, networking, security settings, and so on. The services 324 may provide other common services for the other software layers. The drivers 326 are responsible for controlling or interfacing with the underlying hardware. For instance, the drivers 326 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 320 provide a common infrastructure that is used by the applications 316 and/or other components and/or layers. The libraries 320 provide functionality that allows other software components to perform tasks in an easier fashion than to interface directly with the underlying operating system 302 functionality (e.g., kernel 322, services 324 and/or drivers 326). The libraries 320 may include system libraries 344 (e.g., C standard library) that may provide functions such as memory allocation functions, string manipulation functions, mathematical functions, and the like. In addition, the libraries 320 may include API libraries 346 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 320 may also include a wide variety of other libraries 348 to provide many other APIs to the applications 316 and other software components/modules.

The frameworks/middleware 318 (also sometimes referred to as middleware) provide a higher-level common infrastructure that may be used by the applications 316 and/or other software components/modules. For example, the frameworks/middleware 318 may provide various graphic user interface (GUI) functions 342, high-level resource management, high-level location services, and so forth. The frameworks/middleware 318 may provide a broad spectrum of other APIs that may be utilized by the applications 316 and/or other software components or modules, some of which may be specific to a particular operating system or platform.

The applications 316 include built-in applications 338 and/or third-party applications 340. Examples of representative built-in applications 338 may include, but are not limited to, a contacts application, a browser application, a book reader application, a location application, a media application, a messaging application, and/or a game application. Third-party applications 340 may include any application developed using the ANDROID™ or IOS™ software development kit (SDK) by an entity other than the vendor of the particular platform and may be mobile software running on a mobile operating system such as IOS™, ANDROID™, WINDOWS® Phone, or other mobile operating systems. The third-party applications 340 may invoke the API calls 308 provided by the mobile operating system (such as operating system 302) to facilitate functionality described herein.

The applications 316 may use built-in operating system functions (e.g., kernel 322, services 324 and/or drivers 326), libraries 320, and frameworks/middleware 318 to create user interfaces to interact with users of the system. Alternatively, or additionally, in some systems, interactions with a user may occur through a presentation layer, such as presentation layer 314. In these systems, the application/component "logic" can be separated from the aspects of the application/component that interact with a user.

Some software architectures use virtual machines. In the example of FIG. 3, this is illustrated by a virtual machine 310. The virtual machine 310 creates a software environment where applications/components can execute as if they were executing on a hardware machine (such as the machine 400 of FIG. 4, for example). The virtual machine 310 is hosted by a host operating system (operating system (OS) 336 in FIG. 3) and typically, although not always, has a virtual machine monitor 360, which manages the operation of the virtual machine 310 as well as the interface with the host operating system (i.e., operating system 302). A software architecture executes within the virtual machine 310 such as an operating system (OS) 336, libraries 334, frameworks 332, applications 330 and/or presentation layer 328. These layers of software architecture executing within the virtual machine 310 can be the same as corresponding layers previously described or may be different.

Figure 4:
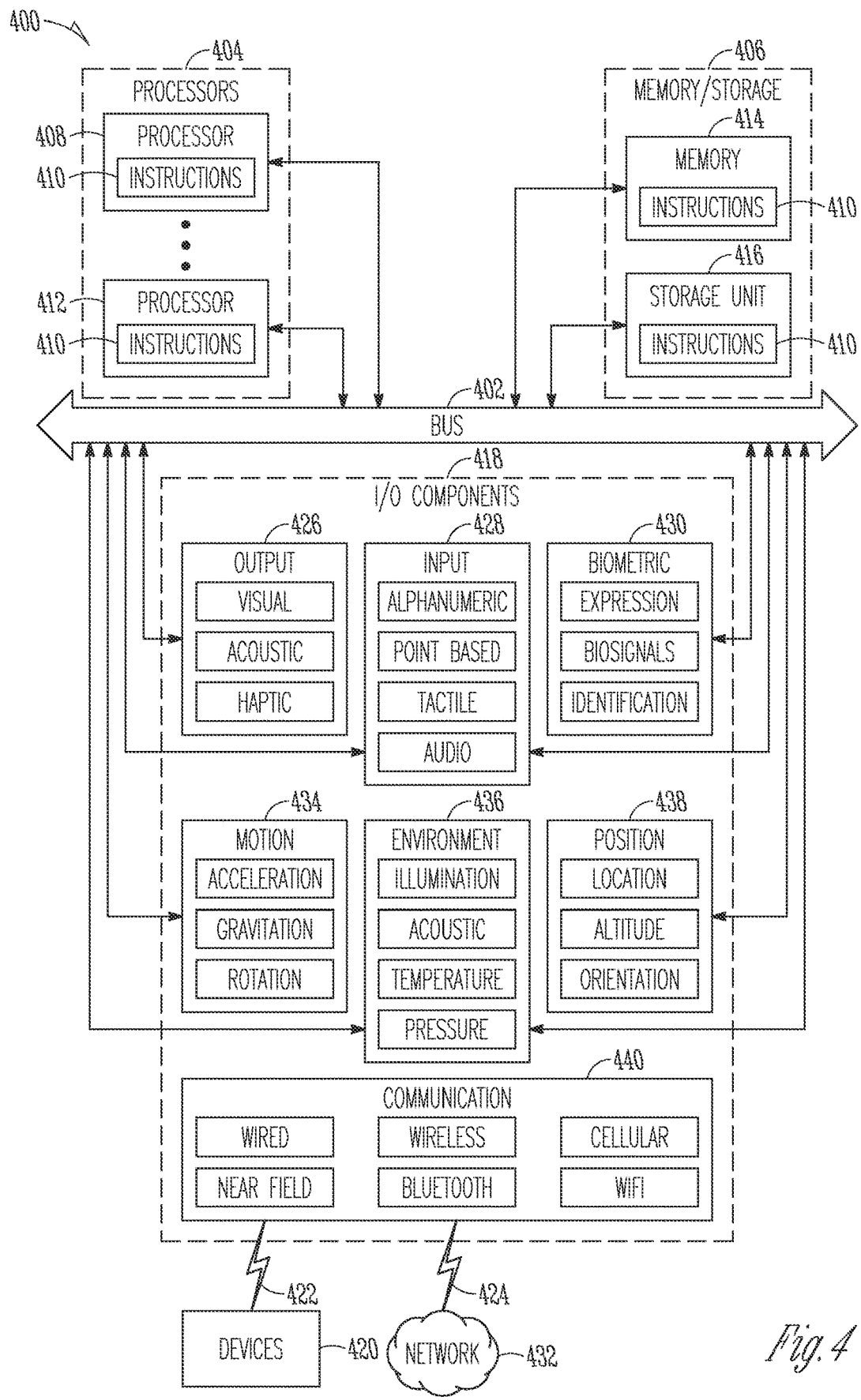
FIG. 4 is a block diagram illustrating components of a machine, according to some example embodiments, able to read instructions from a machine-readable medium (e.g., a machine-readable storage medium) and perform any one or more of the methodologies discussed herein.

FIG. 4 is a block diagram illustrating components of a machine 400, according to some example embodiments, able to read instructions from a machine-readable medium (e.g., a machine-readable storage medium) and perform any one or more of the methodologies discussed herein. Specifically, FIG. 4 shows a diagrammatic representation of the machine 400 in the example form of a computer system, within which instructions 410 (e.g., software, a program, an application, an applet, an app, or other executable code) for causing the machine 400 to perform any one or more of the methodologies discussed herein may be executed. As such, the instructions 410 may be used to implement modules or components described herein. The instructions 410 transform the general, non-programmed machine into a particular machine programmed to carry out the described and illustrated functions in the manner described. In alternative embodiments, the machine 400 operates as a standalone device or may be coupled (e.g., networked) to other machines. In a networked deployment, the machine 400 may operate in the capacity of a server machine or a client machine in a server-client network environment, or as a peer machine in a peer-to-peer (or distributed) network environment. The machine 400 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 410, sequentially or otherwise, that specify actions to be taken by machine 400. Further, while only a single machine 400 is illustrated, the term "machine" shall also be taken to include a collection of machines that individually or jointly execute the instructions 410 to perform any one or more of the methodologies discussed herein.

The machine 400 may include processors 404, memory/storage 406, and I/O components 418, which may be configured to communicate with each other such as via a bus 402. The memory/storage 406 may include a memory 414, such as a main memory, or other memory storage, and a storage unit 416, both accessible to the processors 404 such as via the bus 402. The storage unit 416 and memory 414 store the instructions 410 embodying any one or more of the methodologies or functions described herein. The instructions 410 may also reside, completely or partially, within the memory 414, within the storage unit 416, within at least one of the processors 404 (e.g., within the processor's cache memory), or any suitable combination thereof, during execution thereof by the machine 400. Accordingly, the memory 414, the storage unit 416, and the memory of processors 404 are examples of machine-readable media.

The I/O components 418 may include a wide variety of components to receive input, provide output, produce output, transmit information, exchange information, capture measurements, and so on. The specific I/O components 418 that are included in a particular machine will depend on the type of machine. For example, portable machines such as mobile phones will likely include a touch input device or other such input mechanisms, while a headless server machine will likely not include such a touch input device. It will be appreciated that the I/O components 418 may include many other components that are not shown in FIG. 4. The I/O components 418 are grouped according to functionality merely for simplifying the following discussion and the grouping is in no way limiting. In various example embodiments, the I/O components 418 may include output components 426 and input components 428, The output components 426 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 428 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 418 may include biometric components 430, motion components 434, environment components 436, or position components 438 among a wide array of other components. For example, the biometric components 430 may include components to detect expressions (e.g., hand expressions, facial expressions, vocal expressions, body gestures, or eye tracking), measure bio signals (e.g., blood pressure, heart rate, body temperature, perspiration, or brain waves), identify a person (e.g., voice identification, retinal identification, facial identification, fingerprint identification, or electroencephalogram based identification), and the like. The motion components 434 may include acceleration sensor components (e.g., accelerometer), gravitation sensor components, rotation sensor components (e.g., gyroscope), and so forth. The environment components 436 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 438 may include location sensor components (e.g., a Global Position System (UPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 418 may include communication components 440 operable to couple the machine 400 to a network 432 or devices 420 via coupling 424 and coupling 422, respectively. For example, the communication components 440 may include a network interface component or other suitable device to interface with the network 432. In further examples, communication components 440 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 420 may be another machine or any of a wide variety of peripheral devices (e.g., a peripheral device coupled via a Universal Serial Bus (USB)).

Moreover, the communication components 440 may detect identifiers or include components operable to detect identifiers. For example, the communication components 440 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 440, such as location via Internet Protocol (IP) geo-location, location via Wi-Fi® signal triangulation, location via detecting a NFC beacon signal that may indicate a particular location, and so forth.

Referring again to FIG. 2, the medical data aggregation and presentation system 106 addresses the problems described above in the following way. The diagnostic workflow component 300 automatically reviews the patient's entire medical record to extract pertinent information, diagnose conditions, and document these on behalf of physicians. In some examples, the diagnostic workflow component 300 uses a mix of expert systems and natural language processing (NLP) to find these diagnoses and create the relevant medical notes for a physician.

In some examples, the medical data aggregation and presentation system 106 acts as an expert system and performs diagnostic work, while also driving towards an analysis of the more common conditions a physician will seek to treat. Specific algorithms or routines as described herein have been developed to perform this diagnosis. Further algorithms determine, based on the data and patterns in a patient's medical record, how to write a medical note for a physician and medical staff. Examples of the medical data aggregation and presentation system 106 provides actionable data made readily accessible by an improved user interface. The data is provided in a format that a doctor and medical staff recognize (i.e. as medical or bed notes) in a directly editable form that allows the doctor or staff to add notes or override or edit a suggested diagnosis as needed, while seeking to minimize the tedious conventional data-review work that a physician is typically required to complete every day.

Figure 5:
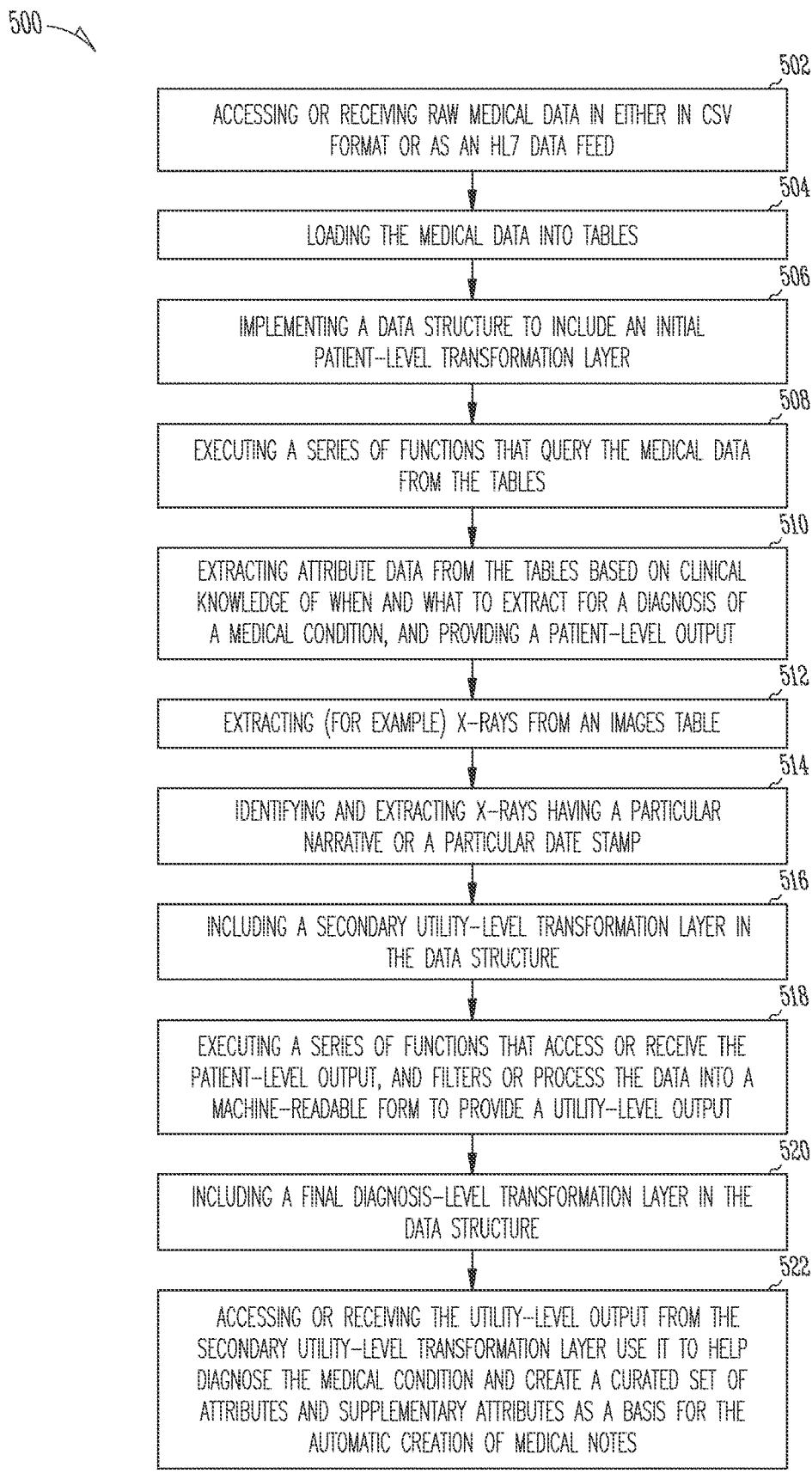
FIG. 5 is a flowchart for a method, in accordance with an example embodiment.

In some examples, with reference to FIG. 5, the diagnostic workflow component 300 performs some or all of the illustrated operations in an example method 500 for creating medical notes for a physician and presenting them in an improved user interface. The method 500 comprises, at operation 502, accessing or receiving raw medical data via csv format, HL7 data feed (a healthcare specific data transfer), FHIR, or $3^{rd}$ party systems such as Sansoro or Redox; at operation 504, loading the medical data into standard data storage tables; at operation 506, implementing a data structure to include an initial patient-level transformation layer by executing, at operation 508, a series of functions that query the medical data from the data storage tables, transforms it into a standardized data format, and, at operation 510, extracts attribute data from the tables based on clinical knowledge of when and what to extract for a diagnosis of a medical condition, and providing a patient-level output. The clinical knowledge may be based on human input or derived from an expert system, such as a trained machine. For example, in order to diagnose pneumonia, operation 510 may include in operation 512 extracting chest x-rays from an images table and, more particularly, at operation 514 identifying and extracting X-rays having a particular narrative or a particular date stamp, or both.

The method 500 may also include, at operation 516, including a secondary utility-level transformation layer in the data structure, Operation 516 may further comprise, in operation 518, performing a series of functions that access or receive the patient-level output (for example, as an open-source pandas data frame), and filters or processes the data into a machine-readable form and providing a utility-level output. For example, to continue with the pneumonia example, operation 518 may include creating a supplementary attribute by accessing or receiving an X-ray narrative and apply specific logic to pull out keywords to determine if the X-ray narrative contains positive or negative indications of keywords relevant for pneumonia and is hence germane to this medical condition for presentation as an image in conjunction with an improved user interface described further below.

The method 500 may also comprise, at operation 520, including a final diagnosis-level transformation layer in the data structure. Operation 520 may include, at operation 522, accessing or receiving the utility-level output from the secondary utility-level transformation layer (typically some type of python data structure) and use it to help diagnose the medical condition and create a created set of attributes and supplementary attributes as a basis for the automatic creation of medical notes, accordingly. Returning to the pneumonia example, upon completion of the secondary layer operations described above, a list of positive/negative keywords has been created. The list is used in conjunction with other data inputs to determine if the patient is positive for pneumonia, and how to document it appropriately in an improved user interface. An example output may be: "Probable pneumonia; chest x-ray indicates 'infiltrate' on (Feb. 25, 2018)".

With reference to FIGS. 6A-6B, an example flow chart of a partially automated method 600 for diagnosing a medical condition, for example hypokalemia, is provided. In some examples, the method 600 employs a hybrid approach which may include automated and manual operations to derive a prima facie or initial diagnosis and generates, by a machine, an output in the form of medical notes. The output, or initial diagnosis included in the medical notes, may be amended by a physician reviewing the medical notes in the light, for example, of the physician's experience, other data, or other factors that have come to light since the medical notes were generated, for example. The medical notes are presented electronically in some examples in an improved user interface as described more fully below. In some examples, the medical notes summarize attributes and supplementary attributes relating to a medical condition, in this case hypokalemia.

At operation 602, the name of a medical condition, in this case hypokalemia, is given. At operation 604, a brief summary of the medical condition is provided. At operation 606, diagnostic codes for the medical condition hypokalemia are identified. In this case the diagnostic codes are ICD10:E87.6 and ICD9: 276.8. At operation 608, a diagnosis recommendation is provided. In this example, the diagnosis recommendation is "Get the lab value from a CMP/BMP/RENAL function test within the last 24 hours K<3.5" in other words for potassium levels lower than 3.5. At operation 610, certain properties of the medical condition are identified for inclusion in the medical notes. In this example, the properties relate to mild to moderate, or severe, levels of potassium in a patient's blood level.

At operation 612, further assessment notes for presentation and documentation in the medical notes are generated. For example, the potassium value and date of a test taken in that regard may be identified in documentation to be presented to a physician reading the medical notes. Further, a draft recommendation generated for the physician may include "consider holding all active diuretics that patient is actively taking which may be contributing to hypokalemia". Examples of such active diuretics are then listed ranging from chlorothiazide (Diuril) to torsemide (Demadex). The listing may act as a mental prompt to the physician to check these aspects in the patient's medication. At operation 614, general notes are identified and in this example are expressed in the form of operations that are understood by a machine, for example "if low phosphate show low phosphate that value and date", and for example, "if low magnesium show low magnesium that value and date". At operation 616, content values for a chart are identified, in this case potassium, magnesium, and phosphorus values, At operation 618, a further recommendation is prepared for the physician in the form of a note plan, in this example "recommend replacing electrolyte for low K, pH, and Mg". At operation 620, values for these three graph components are provided, with a further recommendation for example "do hypo/hyper—magnesemia and phosphatemia". At operation 622, a note of potential issues is generated, in this case relating for example to a magnesium component, as illustrated.

With reference to FIGS. 7A-7B, an example flow chart of a partially automated method 700 for diagnosing a medical condition, for example respiratory failure, is provided. In some examples, the method 700 employs a hybrid approach which may include automated and manual operations to derive a prima facie or initial diagnosis and generates, by a machine, an output in the form of medical notes. The output, or initial diagnosis included in the medical notes, may be amended by a physician reviewing the medical notes in the light of, for example, the physician's experience, other data, or other factors that have come to light since the medical notes were generated, for example. The medical notes are presented electronically in some examples in an improved user interface as described more fully below. In some examples, the medical notes summarize attributes and supplementary attributes relating to a medical condition, in this case respiratory failure.

At operation 702, the name of a medical condition, in this case respiratory failure, is given. At operation 704, a background to the medical condition is provided. The background includes that operation 706, a machine name for example resp_failure. At operation 708, a human readable name is provided, in this case, "respiratory failure". At operation 710, a list of positive diagnoses is generated. For example, the list of diagnoses may include hypoxemic respiratory failure, hypercapneic respiratory failure, and hypoxemic respiratory and hypercapneic respiratory failure. The list 710 may include a recommendation to add in acute, chronic, or acute on chronic medical conditions.

At operation 712, certain ICD diagnostic codes for the medical condition respiratory failure are identified. The ICD codes may include codes for the acute, chronic, and acute on chronic phases of the medical condition, as illustrated. At operation 714, a diagnostic pathway is generated. For example, at operation 716, the diagnostic pathway 714 may include checking lab values from tests taken within an identified time frame, for example the most recent ABG test taken within 48 hours. Operation 718 may include a determination of whether the medical condition (in this case respiratory failure) is acute, chronic or acute on chronic. This determination may include looking at aspects such as an Acute Kidney Injury module, and diagnostic flags relating, for example, to the functioning of a patient's kidneys or a higher-than-baseline PaCO$_2$. At operation 720, the diagnostic pathway 714 may include the identification of possible causes, for example hypoxemic causes such as pneumonia, acetelectasis, Congestive Heart Failure, and Acute Respiratory Distress Syndrome. Other causes 720 may include hypercapneic causes, such as decreased respiratory drive from sedatives, respiratory muscle weakness from neuro-muscular disease, scoliosis, and obstructive lung diseases like asthma, Chronic Obstructive Pulmonary Disease, and Acute Respiratory Distress Syndrome. At operation 722, operations that are readable by a machine are identified. For example, at operation 724, a machine may be instructed to include an acute, chronic, or acute on chronic phase in the name of the medical condition. At operation 726, the machine may be instructed to add a chart. Further, the machine may be instructed to use data for the past week, on the basis of an identified item of data or a data point. At operation 728, a machine may be instructed to monitor a given condition and recommend drugs for inclusion in a medication regimen via a utility-layer function (operation 516), for example. At operation 730, possible causes for the medical condition may be identified. Thus, in some examples, there is provided a computing apparatus comprising a processor and a memory storing instructions that, when executed by the processor, configure the apparatus to access first patient data relating to a first medical condition, the first patient data including a first set of attributes relating to the first medical condition; access second patient data relating to a second medical condition, the second patient data including a second set of attributes relating to the second medical condition; combining the first and second patient data into a patient data structure that includes the first and second sets of attributes relating to the first and second medical condition; and generating first and second sets of supplementary attributes relating to the respective first and second sets of attributes.

Some embodiments include machine-readable media including instructions which, when read by a machine, cause the machine to perform the operations of any one or more of the methods described herein.

As mentioned further above, the application 104 also provides a number of user interfaces, which present output of certain operations as described herein to a user of the client device 108. The operations may include one or more of the operations described with reference to FIGS. 5-7, or elsewhere in the specification. Referring now to FIGS. 8A-8C, an example of an improved user interface 800 is described. Corresponding interface elements are the same or similar in each view. As mentioned above, first and second patient data is combined into a patient data structure that includes first and second sets of attributes relating to respective first and second medical condition. First and second sets of supplementary attributes relating to the respective first and second sets of attributes are also generated and form part of the data structure in some examples. A user interface, such as the user interface 800, is generated to present, as described below, the attributes and supplementary attributes in the form of editable medical notes that may be reviewed and edited by a physician or hospital medical staff, for example.

In each of the views of the user interface 800 shown in FIGS. 8A-8C, first and second sets of attributes relating to first and second medical conditions are presented as notes in the user interface 800. In this example, attributes and supplementary attributes relating to six such medical conditions are presented. For example, a first medical condition relates to congestive heart failure 802. A second medical condition relates to chronic kidney injury, stage 5 shown at 804. A third medical condition relates to an example pulmonary disease 806. A fourth medical condition relates to diabetes mellitus, type II (uncontrolled). A fifth medical condition relates to hyperlipidemia 810. A sixth medical condition relates to hypertension 812.

The presentation of attributes and supplementary attributes in the user interface 800 comprises at least a presentation, in a first display zone 814 of the user interface 800, a first view including at least one attribute 816A from a first set of attributes 816 relating to the first medical condition, in this case congestive heart failure 802. The set of attributes 816 includes in this example, as illustrated, an elevated BNP, a continued use of a medication (carvedilol), holding of a medication (metoprolol), strict I/O's, and the taking of daily weights. Similar sets of attributes for the other medical conditions 804-812 are shown in the user interface 800. For example, a set of attributes 818 for the second medical condition relating to chronic kidney injury, stage 5, two attributes are displayed. The first attribute indicates the avoidance of nephrotoxic agents, and the second attribute recommends monitoring the medical condition. A set of eleven attributes 820 ranging from a most recent hemoglobin level to a recommendation for monitoring a condition appears for the third medical condition of diabetes mellitus, Type II, 808. The fourth and fifth medical conditions of hyperlipidemia 810 and hypertension 812 respectively are also associated with attributes, as shown.

With reference now to FIG. 9, the presentation of attributes and supplementary attributes in the user interface 800 also includes, in a second display zone 922 of the user interface 800, a first supplementary view including at least one supplementary attribute 924 from a first set of supplementary attributes relating to the first medical condition congestive heart failure 802. Here, the example supplementary attribute relating to the congestive heart failure 802 is a previous diagnosis of heart failure 924. In this case, the first set of supplementary attributes is a set comprising one supplementary attribute 924. Similar supplementary views for the medical conditions of chronic kidney injury, stage 5 804, and pulmonary disease 806, are provided in the view. The illustrated supplementary attributes for the chronic kidney injury 804 are listed in a set of supplementary attributes 92A-924D which appear above the previously displayed attributes 818 in FIG. 8A. In the views shown in FIGS. 8A-8C, no attributes for the third medical condition pulmonary disease 806 are shown. In the view given in FIG. 9, however, a supplementary attribute 926 relating to previous diagnoses of chronic obstructive coronary disease (unspecified), other pulmonary disease, chronic obstructive pulmonary disease with acute lower respiratory infection, is provided.

In each of the views of FIGS. 8A-8C and FIG. 9 a presentation of a toggle feature 850 is provided. The user interface 800 or the toggle feature 850 is configured to appear to "move" between a location adjacent the display of the first medical condition 802 (FIG. 8A), to a location adjacent the display of the second medical condition 804 (FIG. 8B) a location adjacent to the third medical condition 806 (FIG. 8C). The toggle element 850 is selectable at sub-element 851 by a user to toggle between the presentations of the first views of the attributes relating to medical conditions as shown in FIGS. 8A-8C, and the respective first supplementary views of supplementary attributes of these medical conditions as shown in FIG. 9. Although not shown in the views, the toggle element 850 is also "movable" in the user interface standard to locations adjacent the fourth, fifth, and sixth medical condition 808-812, respectively.

Thus, the presentation of attributes and supplementary attributes of medical conditions in the user interface 800 further comprises presentation, in a third display zone (for example the zone of the user interface 800 containing the set of attributes 816, or the zone containing the set of attributes 8204 the medical condition of diabetes mellitus, type of the user interface 800, a third view including at least one attribute 818 from a second set of attributes 816 relating to the second medical condition 804, and wherein the toggle element 850 is configured to appear to move, under the input or guidance of a pointing device, between respective locations at or adjacent the first and third display zones of the user interface (for example, locations adjacent the names of the medical conditions 802-806.

Turning again to FIG. 9, the presentation of attributes and supplementary attributes in the user interface 800 further comprises presentation, in a fourth display zone 922 (or the display zones containing the supplementary attributes 924, and 926) of the user interface 800, a second supplementary view including at least one supplementary attribute, for example supplementary attribute 924A, from the second set of supplementary attributes 924 relating to the second medical condition, for example the chronic kidney injury stage 5, 804. The user interface 800 or the toggle element 850 is configured to toggle, at each respective location adjacent the name of a medical condition, between the presentations of the attribute views visible in FIGS. 8A-8C and the more detailed respective supplementary attribute views provided in the user interface 800 of FIG. 9, respectively. In some examples, toggle element 850 can also be used to re-order medical conditions. For example, by clicking on a sub-element 853 of toggle element 850 and dragging, the first medical condition can swap positions with the second medical condition, allowing the physician the flexibility to prioritize each medical condition. In some examples, the toggle element 850 also has a sub-element 855 within it that allows the physician to remove the condition if they deem it inaccurate.

In some examples, the listed attributes and supplementary attributes are provided in the form of medical notes which are directly editable by a user in the user interface to edit at least one of the first, first supplementary, second, and second supplementary views. In some examples, the first, first supplementary, second, and second supplementary views are visible simultaneously in the user interface. An example of this arrangement appears in FIG. 9.

Figure 11:
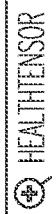
FIG. 11 shows an example Vitals view in an example user interface, in accordance with an example embodiment.

It will be noted that in the top right-hand corner of the view of the user interface 800 shown in FIG. 8A that a "Notes" view 852 and a "Record" view 854 are selectable via links. Example sub-views accessible via the Record 854 link include a "Labs" view 1000 (FIG. 10), a "Vitals" view 1100 (FIG. 11), a "Meds" view 1200 (FIG. 12), and an "Imaging" view 1300 (FIG. 13). Each of these views contains salient details of a patient's medical data as shown. The data contained in these views may be used to supplement or edit the medical notes shown in FIGS. 8A-8C or FIG. 9 as needed, or as results underlying a given diagnosis or prognosis. Thus, the supporting sets of data such as the borrower to rework vital signs, medication and images are readily convenient and provided in one place for reference by a physician, or hospital medical staff for example.

In some examples, the first or second supplementary view includes a graph depicting aspects relating to an attribute or supplementary attribute of the first or second medical condition. With reference to FIGS. 8A-8C, the toggle element 850 may be moved under the guidance of a pointing device such as a mouse for example to a location adjacent the fourth medical condition diabetes mellitus, type II 808. At this location, the toggle element 850 may be selected by a user operating the mouse to cause the display in the user interface 800 of one or more graphs relating to an attribute or supplementary attribute of this medical condition. An example of such a graph 1400 appears in FIG. 14.

Figure 15:
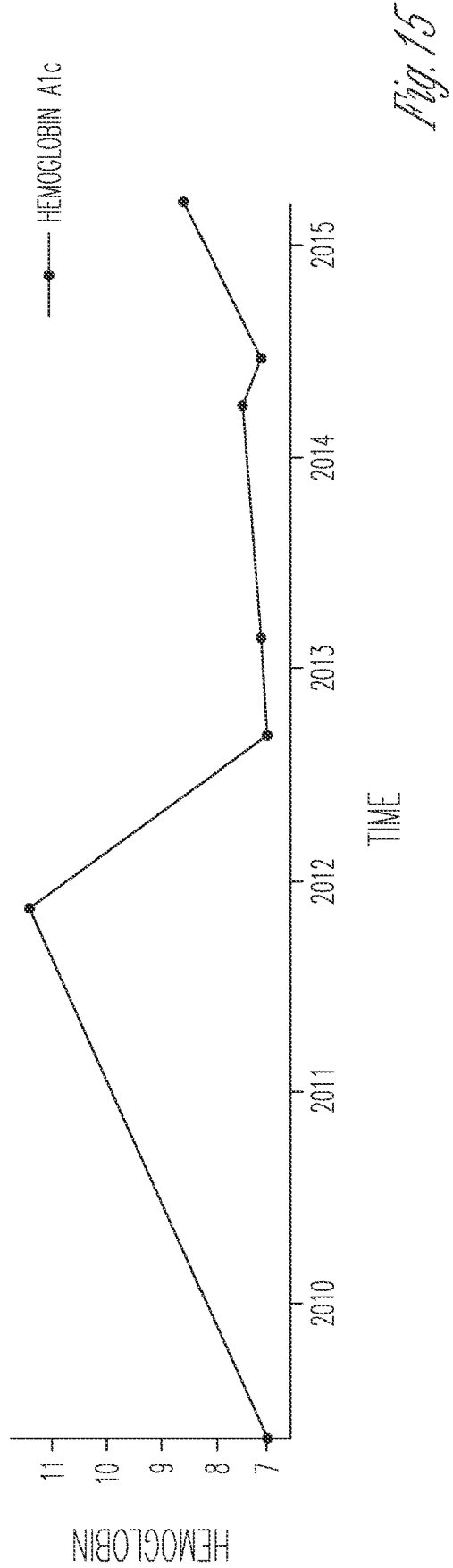
Figure 16:
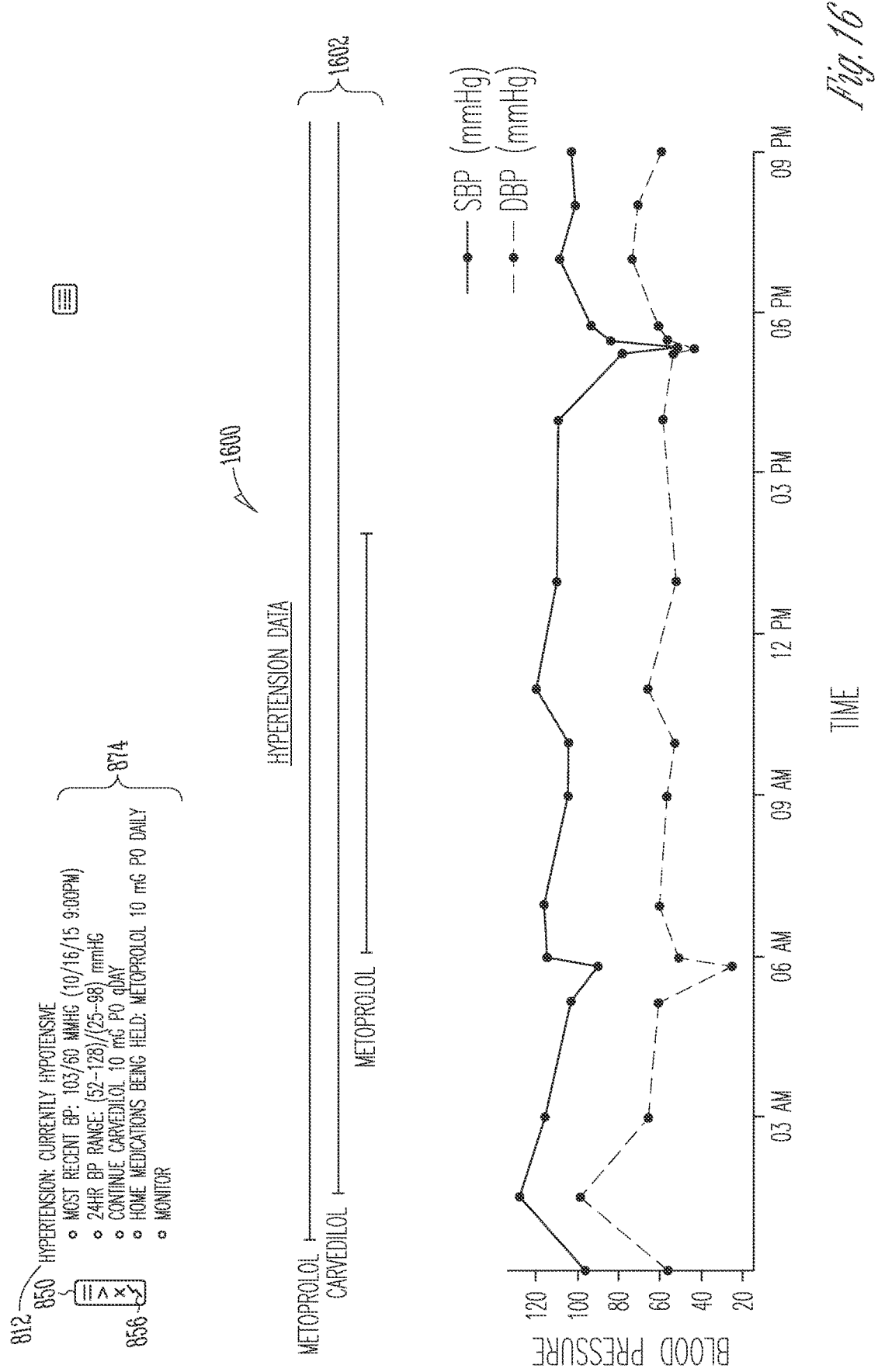
Figure 17:
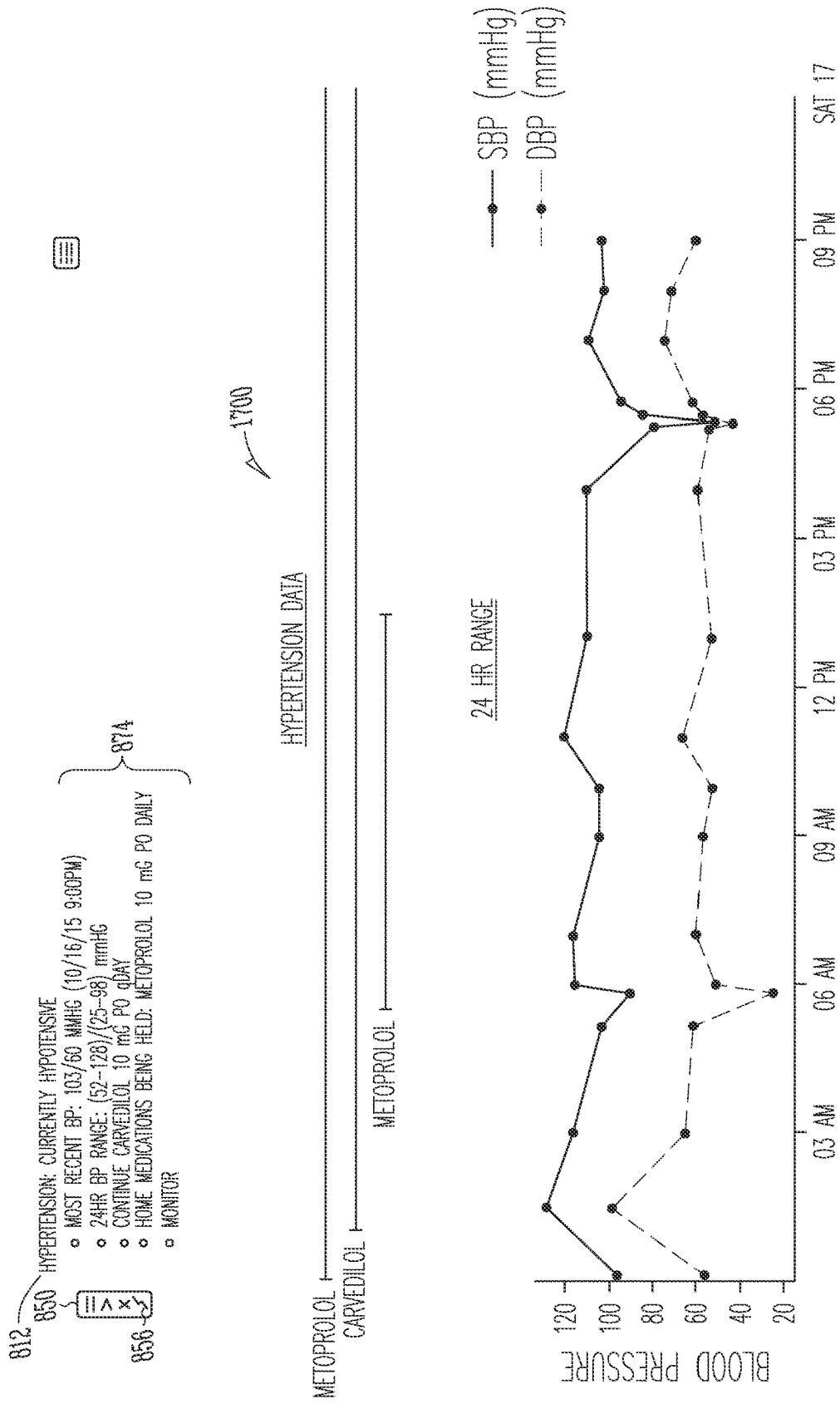

A user may be prompted to cause display of the graph 1400 by an icon 856 visible on the toggle element 850. The icon 856 renders the user aware that supplementary attributes, in the form of graph, are obtainable for presentation in the user interface 800. About the graph 1400), the set of attributes 820 is still visible in the view. A presentation of the graph 1400 may also be obtained by a user by clicking on the link 858 (>180 mg/dL). A presentation of a second graph 1500 visible in FIG. 15 may be obtained by clicking on the link 860 labeled 8.6% (Mar. 18, 2015 5.50 pm), Thus, supplementary views containing the graph 1400 or the graph 1500 selectively appearing below the set of attributes 820 relating to the fourth medical condition diabetes mellitus, type II 808, are provided. In some examples, further toggling of the toggle element 850 causes the graphs 1400 and 1500 to appear in sequential order one after the other, or to be removed from display in the user interface 800.

With reference again to FIG. 14, the graph 1400 relates to the attribute 820 with which the link 858 is associated. In this case, graphical results are displayed relating to the attribute of blood glucose over the last 24 hours. An elevated level is noted in the associated attribute 820. Should a physician, for example, reading the medical notes which include the set of attributes 820 relating to the fourth medical condition diabetes mellitus type II disagree that the indicated blood glucose levels are elevated, the associated attribute may be edited with a note that the glucose levels are "not elevated". Further, any one or more of the attributes 820 relating for example to continuing a given medication may be edited to read "discontinue". Thus, the medical notes provided in the user interface 800 are directly editable in the user interface 800 without having to navigate, for example, to another screen or to make a note in a separate diary or logbook as is often the case conventionally.

Figure 14:
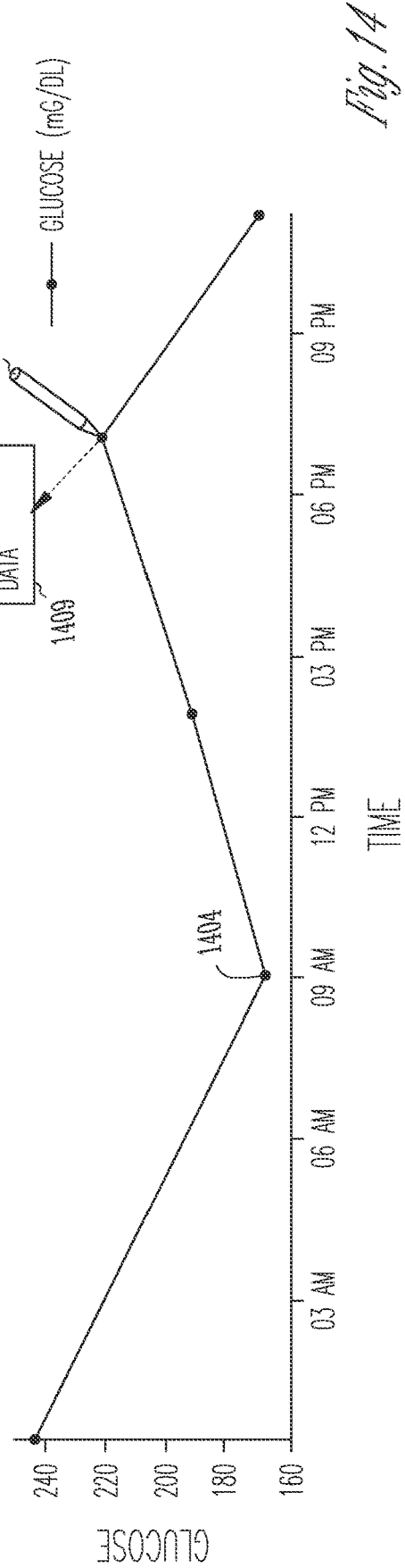
FIGS. 14-17 show views in example user interfaces, in accordance with example embodiments.

The graph 1400 in FIG. 14 also includes a time-based representation 1402 of a medication regimen which is temporally synchronous with the depicted aspect relating to the attribute or supplementary attribute of the first or second medical condition. If a pointing device (e.g., a finger, or a mouse) is placed over any part of 1402, a tooltip 1403 appears, showcasing in a data window 1405 in the interface details of the medication. Details may include for example a medication name, a start time, a stop time, a route, and a dosage. The aspect depicted for the attribute in the graph 1400 is a blood glucose level, in this case a blood glucose level over the last 24 hours. This attribute relates to the fourth medical condition of diabetes mellitus, type II 808. The medication regimen to address this attribute of the medical condition 808 includes, as shown, insulin, pregabalin, metformin, and tolbutamide. In this example, the graph 1400 shows that these medications were administered just before 6 AM of a given morning. An effect of these medications may be seen by the decreased blood glucose level indicated at data point 1404. Additionally, if a pointing device is placed over the point 1404, a tooltip 1407 appears, showcasing in a data window 1409 in the interface salient details of medication or other diagnostic information germane to that point. Details may include for example a point type and a date. Thus, a physician is provided supplementary attributes or data directly in the user interface 800, with an indication of what effect a given regimen of medication may be having on a patient for whom the medical notes have been formulated.

Returning again to FIG. 8A, further supplementary views of graphical data, or supplementary attributes, may be obtained by clicking on the links 870 and 872. The link 870 has a descriptive label "103/60 mmHg (Oct. 16, 2015 9.00 PM) indicative of a recent blood pressure and time with which the attribute is associated. As shown, a most recent blood pressure is one of the attributes in the set of attributes 812. Selecting the link 870, causes presentation of a graph 1600 visible below the set of attributes 874 relating to the sixth medical condition of hypertension 812. The set of attributes 812 is visible both in the views of FIGS. 8A-8C, and FIG. 16. The graph 1600 provides a supplementary view of supplementary attributes in conjunction with the set of attributes and more of this information is visible simultaneously in the user interface 800. Here too, details of medications in a medication regimen and associated timing of administration of these medications is provided at 1602. The effects of these medications on a patient may be seen in the section of the graph 1600 appearing below the medication regimen 1602. Selecting the link 872 in FIG. 8A, causes presentation of a chart 1700 which is made visible in the interface beneath the same set of hypertension attributes 874. Thus, in some examples, two charts 1600 and 1700 and associated data can be accessed and rendered visible at any time. Other types and numbers of charts are possible. The data provided in graph 1700 is based on 24-hour period. Thus, it will be noted that the units displayed on the horizontal axis of graph 1700 are presented over a full day, whereas similar units shown in graph 1600 are presented for a shorter period.

In some examples, the data relating to the displayed attributes and supplementary attributes in the various views is derived from an assembled data structure, as described more fully about. Combining the first and second patient data into a patient data structure may include at least extracting attribute data from a table based on an assigned relevance of that data to a diagnosis of a medical condition; correlating the extracted attribute data with a report from a diagnostic report; and generating a supplementary attribute by identifying a narrative or date stamp associated with the report based on the medical condition.

Figure 18:
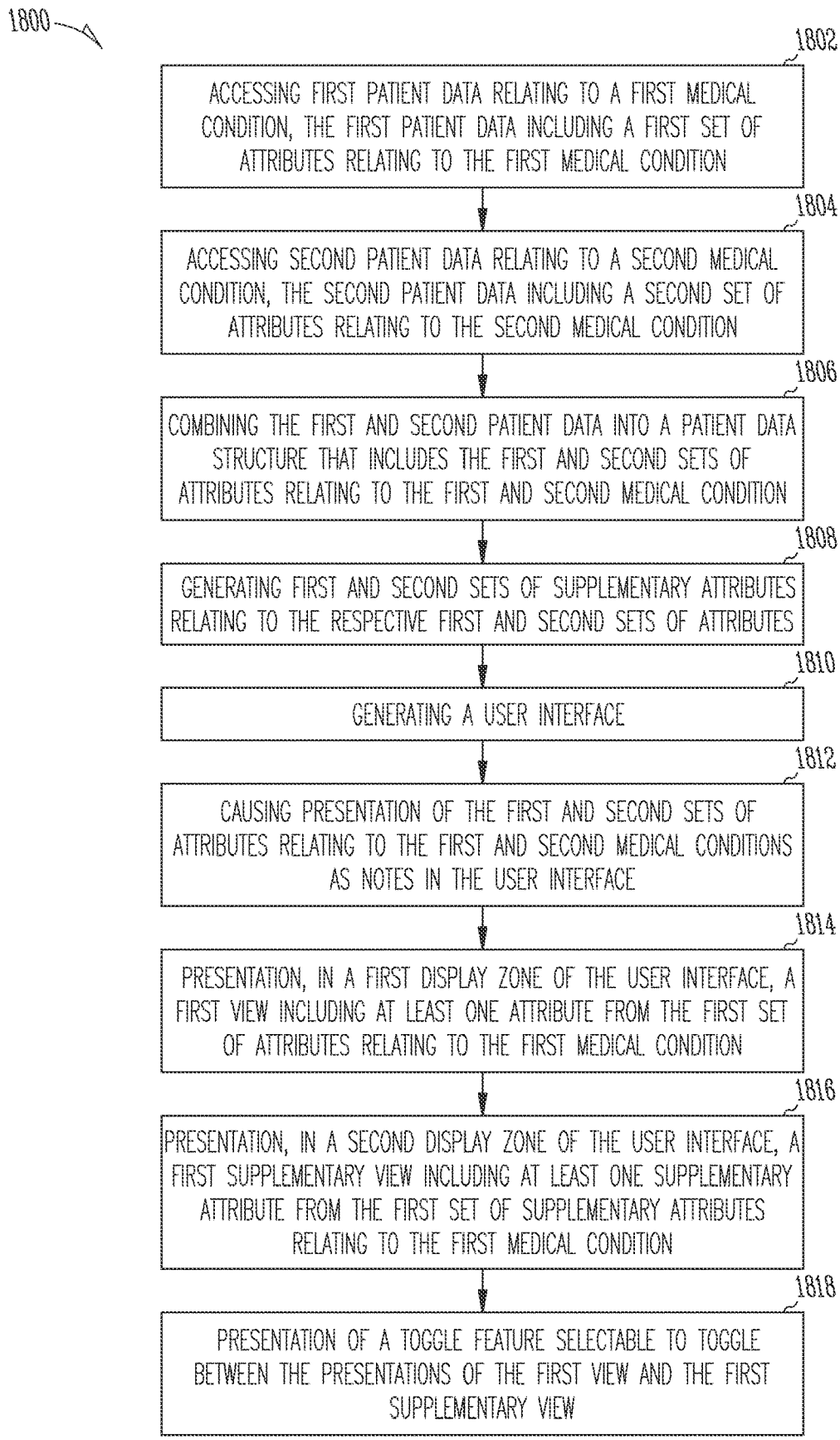
FIG. 18 is a flowchart for a method, in accordance with an example embodiment.

Thus, with reference to FIG. 18, an example method 1800 may comprise, at operation 1802, accessing first patient data relating to a first medical condition, the first patient data including a first set of attributes relating to the first medical condition; at operation 1804, accessing second patient data relating to a second medical condition, the second patient data including a second set of attributes relating to the second medical condition; at 1806, combining the first and second patient data into a patient data structure that includes the first and second sets of attributes relating to the first and second medical condition; at 1808, generating first and second sets of supplementary attributes relating to the respective first and second sets of attributes; at 1810, generating a user interface; at 1812, causing presentation of the first and second sets of attributes relating to the first and second medical conditions as notes in the user interface, wherein the presentation comprises, at 1814, presentation, in a first display zone of the user interface, a first view including at least one attribute from the first set of attributes relating to the first medical condition; at 1816, presentation, in a second display zone of the user interface, a first supplementary view including at least one supplementary attribute from the first set of supplementary attributes relating to the first medical condition; and, at 1818, presentation of a toggle feature selectable to toggle between the presentations of the first view and the first supplementary view.

In some examples, the presentation further comprises presentation, in a third display zone of the user interface, a third view including at least one attribute from the second set of attributes relating to the second medical condition, and wherein the toggle element is configured to appear to move, under the input or guidance of a pointing device, between respective locations at or adjacent the first and third display zones of the user interface.

In some examples, the presentation further comprises presentation, in a fourth display zone of the user interface, a second supplementary view including at least one supplementary attribute from the second set of supplementary attributes relating to the second medical condition, and wherein the toggle element is configured to toggle, at each respective location, between the presentations of the first view and the first supplementary view, and the second view and second supplementary view, respectively.

In some examples, the notes are directly editable by a user in the user interface to edit at least one of the first, first supplementary, second, and second supplementary views. In some examples, the first, first supplementary, second, and second supplementary views are visible simultaneously in the user interface. In some examples, the first or second supplementary view includes a graph depicting aspects relating to an attribute or supplementary attribute of the first or second medical condition. In some examples, the graph includes a time-based representation of a medication regimen, the time-based representation temporally synchronous with the depicted aspect relating to the attribute or supplementary attribute of the first or second medical condition.

In some examples, combining the first and second patient data into a patient data structure includes, at least: extracting attribute data from a table based on an assigned relevance of that data to a diagnosis of a medical condition; correlating the extracted attribute data with a report from a diagnostic report; and generating a supplementary attribute by identifying a narrative or date stamp associated with the report based on the medical condition.

Although the subject matter has been described with reference to specific example embodiments, it will be evident that various modifications and changes may be made to these embodiments without departing from the broader spirit and scope of the disclosed subject matter. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Description, therefore, is not to be taken in a limiting sense, and the scope of various embodiments is defined only by any appended claims, along with the full range of equivalents to which such claims are entitled.

Such embodiments of the inventive subject matter may be referred to herein, individually and/or collectively, by the term "invention" merely for convenience and without intending to voluntarily limit, the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system comprising:
   at least one processor, and
   executable instructions, being accessible on a computer-readable medium, that when executed, cause the at least one processor to perform operations comprising:
   generating and presenting an interface including a first medical condition, a second medical condition, and a toggle feature, the first medical condition relating to first patient data and having a first set of attributes being listed below the first medical condition, the second medical condition relating to second patient data and having a second set of attributes being listed below the second medical condition, the toggle feature being moveable and including selectable sub-elements thereon including a first selectable sub-element for re-ordering the first and the second medical conditions, a second selectable sub-element for expanding the attributes associated with a medical condition, and a third selectable sub-element for removing the medical condition from the interface;
   receiving first input causing movement of the toggle feature to a position on the interface adjacent to the first medical condition, moving the toggle feature including selecting and guiding the toggle feature with a pointing device;
   receiving a first selection selecting the first selectable sub-element of the toggle feature, the toggle feature being positioned at the first medical condition, and modifying the interface to include a first set of supplementary attributes below the first medical condition responsive to receiving the first selection;
   receiving second input causing movement of the toggle feature to a position on the interface adjacent to the second medical condition;
   receiving a second selection selecting the first selectable sub-element of the toggle feature, the toggle feature being positioned at the second medical condition, and modifying the interface to include a second set of supplementary attributes below the second medical condition responsive to receiving the second selection;
   receiving third input causing movement of the toggle feature to a position on the interface adjacent to a selected medical condition, the selected medical condition being selected from a group of medical conditions including the first medical condition and the second medical condition;
   receiving a third selection selecting the second selectable sub-element of the toggle feature, the toggle feature being positioned at the selected medical condition, and re-ordering the first and second medical conditions responsive to receiving the third selection; and
   receiving a fourth selection selecting the third selectable sub-element of the toggle feature, the toggle being positioned adjacent to the selected medical condition, and removing the selected medical condition from the interface responsive to receiving the fourth selection.

2. The system of claim 1, wherein the interface includes notes that are editable.

3. The system of claim 2, wherein the notes include the first set of attributes, the first set of supplementary attributes, the second set of attributes, and the second set of supplementary attributes.

4. The system of claim 1, wherein the interface further includes a graph depicting aspects relating to a supplementary attribute of the selected medical condition.

5. The system of claim 4, wherein the graph includes a time-based representation of a medication regimen.

6. The system of claim 5, wherein the time-based representation of the medication regimen is temporally synchronous with an aspect relating to the supplementary attribute of the selected medical condition.

7. The system of claim 1, further comprising combining the first patient data and the second patient data into a patient data structure.

8. The system of claim 7, wherein the combining the first patient data and the second patient data into a patient data structure includes extracting attribute data from a table.

9. The system of claim 8, wherein the combining the first patient data and the second patient data into a patient data structure further includes:
   correlating the attribute data with a diagnostic report; and
   generating a supplementary attribute.

10. A method comprising:
    generating and presenting an interface including a first medical condition; a second medical condition, and a toggle feature, the first medical condition relating to first patient data and having a first set of attributes being listed below the first medical condition, the second medical condition relating to second patient data and having a second set of attributes being listed below the second medical condition, the toggle feature being moveable and including selectable sub-elements thereon including a first selectable sub-element for re-ordering the first and the second medical conditions;

a second selectable sub-element for expanding the attributes associated with a medical condition, and a third selectable sub-element for removing the medical condition from the interface;

receiving first input causing movement of the toggle feature to a position on the interface adjacent to the first medical condition, moving the toggle feature including selecting and guiding the toggle feature with a pointing device;

receiving a first selection selecting the first selectable sub-element of the toggle feature, the toggle feature being positioned at the first medical condition, and modifying the interface to include a first set of supplementary attributes below the first medical condition responsive to receiving the first selection;

receiving second input causing movement of the toggle feature to a position on the interface adjacent to the second medical condition;

receiving a second selection selecting the first selectable sub-element of the toggle feature, the toggle feature being positioned at the second medical condition, and modifying the interface to include a second set of supplementary attributes below the second medical condition responsive to receiving the second selection;

receiving third input causing movement of the toggle feature to a position on the interface adjacent to a selected medical condition, the selected medical condition being selected from a group of medical conditions including the first medical condition and the second medical condition;

receiving a third selection selecting the second selectable sub-element of the toggle feature, the toggle feature being positioned at the selected medical condition, and re-ordering the first and second medical conditions responsive to receiving the third selection; and receiving a fourth selection selecting the third selectable sub-element of the toggle feature, the toggle being positioned adjacent to the selected medical condition, and removing the selected medical condition from the interface responsive to receiving the fourth selection.

11. The method of claim 10, wherein the interface includes notes that are editable.

12. The method of claim 11, wherein the notes include the first set of attributes, the first set of supplementary attributes, the second set of attributes, and the second set of supplementary attributes.

13. The method of claim 10, wherein the interface further includes a graph depicting aspects relating to a supplementary attribute of the selected medical condition.

14. The method of claim 13, wherein the graph includes a time-based representation of a medication regimen.

15. The method of claim 14, wherein the time-based representation of the medication regimen is temporally synchronous with an aspect relating to the supplementary attribute of the selected medical condition.

16. The method of claim 10, further comprising combining the first patient data and the second patient data into a patient data structure.

17. The method of claim 16, wherein the combining includes extracting attribute data from a table.

18. The method of claim 17, wherein the combining further includes:
correlating the attribute data with a diagnostic report; and
generating a supplementary attribute.

19. One or more computer-readable hardware storage devices having stored therein a set of instructions which, when executed by the computer, causes the computer to perform operations comprising:

generating and presenting an interface including a first medical condition, a second medical condition, and a toggle feature, the first medical condition relating to first patient data and having a first set of attributes being listed below the first medical condition, the second medical condition relating to second patient data and having a second set of attributes being listed below the second medical condition, the toggle feature being moveable and including selectable sub-elements thereon including a first selectable sub-element for re-ordering the first and the second medical conditions, a second selectable sub-element for expanding the attributes associated with a medical condition, and a third selectable sub-element for removing the medical condition from the interface;

receiving first input causing movement of the toggle feature to a position on the interface adjacent to the first medical condition, moving the toggle feature including selecting and guiding the toggle feature with a pointing device;

receiving a first selection selecting the first selectable sub-element of the toggle feature, the toggle feature being positioned at the first medical condition, and modifying the interface to include a first set of supplementary attributes below the first medical condition responsive to receiving the first selection;

receiving second input causing movement of the toggle feature to a position on the interface adjacent to the second medical condition;

receiving a second selection selecting the first selectable sub-element of the toggle feature, the toggle feature being positioned at the second medical condition, and modifying the interface to include a second set of supplementary attributes below the second medical condition responsive to receiving the second selection;

receiving third input causing movement of the toggle feature to a position on the interface adjacent to a selected medical condition, the selected medical condition being selected from a group of medical conditions including the first medical condition and the second medical condition;

receiving a third selection selecting the second selectable sub-element of the toggle feature, the toggle feature being positioned at the selected medical condition, and re-ordering the first and second medical conditions responsive to receiving the third selection; and receiving a fourth selection selecting the third selectable sub-element of the toggle feature, the toggle being positioned adjacent to the selected medical condition, and removing the selected medical condition from the interface responsive to receiving the fourth selection.

* * * * *